United States Patent
Kobayashi et al.

(10) Patent No.: US 6,380,262 B1
(45) Date of Patent: Apr. 30, 2002

(54) 5-MEMBERED RING COMPOUNDS

(75) Inventors: Eiji Kobayashi, Otsu; Hiromu Ohnogi, Muko; Nobuto Koyama, Uji; Katsushige Ikai, Koka-gun; Hiroaki Sagawa, Kusatsu; Ikunoshin Kato, Uji, all of (JP)

(73) Assignee: Takara Shuzo Co., Ltd., Kyoto (JP)

( * ) Notice: Subject to any disclaimer, the term of this patent is extended or adjusted under 35 U.S.C. 154(b) by 0 days.

(21) Appl. No.: 09/762,265

(22) PCT Filed: Aug. 10, 1999

(86) PCT No.: PCT/JP99/04324

§ 371 Date: Feb. 6, 2001

§ 102(e) Date: Feb. 6, 2001

(87) PCT Pub. No.: WO00/11021

PCT Pub. Date: Mar. 2, 2000

(30) Foreign Application Priority Data

Aug. 19, 1998 (JP) .......................... 10-232746

(51) Int. Cl.⁷ .................. A61K 31/12; C07C 45/00; C01C 61/06
(52) U.S. Cl. .................. 514/690; 568/64; 568/338; 568/379; 562/503
(58) Field of Search .................. 568/64, 338, 379; 562/503; 514/690

(56) References Cited

U.S. PATENT DOCUMENTS 6,177,592 B1 * 1/2001 Koyama et al. ............ 562/503

FOREIGN PATENT DOCUMENTS

| EP | 0 984 011 A1 | 3/2000 |
| JP | 5-310685 A | 11/1993 |
| JP | 10-45618 A | 2/1998 |
| WO | WO98/39291 A1 | 9/1998 |

OTHER PUBLICATIONS

Miyaguchi Shingo et al., "Relationship Between α–Mannosidase and Natural Killer Activity and Glycopeptides of Peripheral Blood Mononuclear Cells in Patients with Liver Cirrhosis or Hepatocellular Carcinoma." Keigo Igaku, vol. 69(2), pp. 335–346., 1992.

* cited by examiner

Primary Examiner—Sreeni Padmanabhan
(74) Attorney, Agent, or Firm—Browdy and Neimark

(57) ABSTRACT

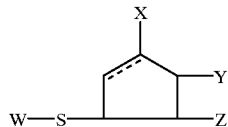

[I]

5-Membered ring compounds represented by general formula (I), optically active isomers thereof or salts of the same. These compounds have physiological activities including a carcinostatic effect. In said formula the bond shown by the dotted line in the 5-membered ring represents that this 5-membered ring may be either a cyclopentene ring having a double bond or a saturated cyclopentane ring, and when the 5-membered ring is a cyclopentene ring, X is $OR_1$, Y is $=O$ and Z is H, and when it is a cyclopentane ring, X is $=O$, Y is $OR_2$ and Z is $OR_3$, (wherein $R_1$ is $R_4$ or $-(CO)-R_5$; $R_2$ is H, $-R_6$ or $-(CO)-R_7$; and $R_3$ is H, $R_8$ or $(CO)-R_9$ (wherein $R_4$, $R_5$, $R_6$, $R_7$, $R_8$ and $R_9$ are the same or different and each represents an aliphatic, aromatic or aliphatic aromatic group, and $R_5$, $R_7$ and $R_9$ may be each H), provided that the case where $R_2=R_3=H$ is excluded); and W represents a residue obtained by eliminating SH from an SH-containing compound.

5 Claims, 7 Drawing Sheets

5-MEMBERED RING COMPOUNDS

This application is a 371 of PCT/JP99/04324 filed Aug. 10, 1999.

1. Technical Field

The present invention relates to a five-membered ring compound having physiological activities such as a carcinostatic activity which is useful in a field of medicine and a method for producing the compound.

2. Background Art

Wide variety of drugs including alkylating agents, antimetabolites, carcinostatics such as vegetable alkaloids, antibiotics, immunoenhancers and immnoregulators are conventionally used for clinical therapies. However, pharmacotherapy using such drugs has not completed yet.

Among these, naturally occurring prostaglandins having α,β-unsaturated carbonyls in their five-membered rings, i.e., prostaglandins A and J, were reported to suppress DNA synthesis, suggesting their possible use as highly safe carcinostatics. Various derivatives thereof were synthesized (see JP-A 62-96438).

OBJECTS OF INVENTION

The main object of the present invention is to develop a compound having physiological activities such as a carcinostatic activity and to provide a method for producing the compound and a pharmaceutical composition containing the compound.

These and other objects as well as advantages of the present invention will be explained below with reference to the attached drawings.

SUMMARY OF INVENTION

Figure 1:
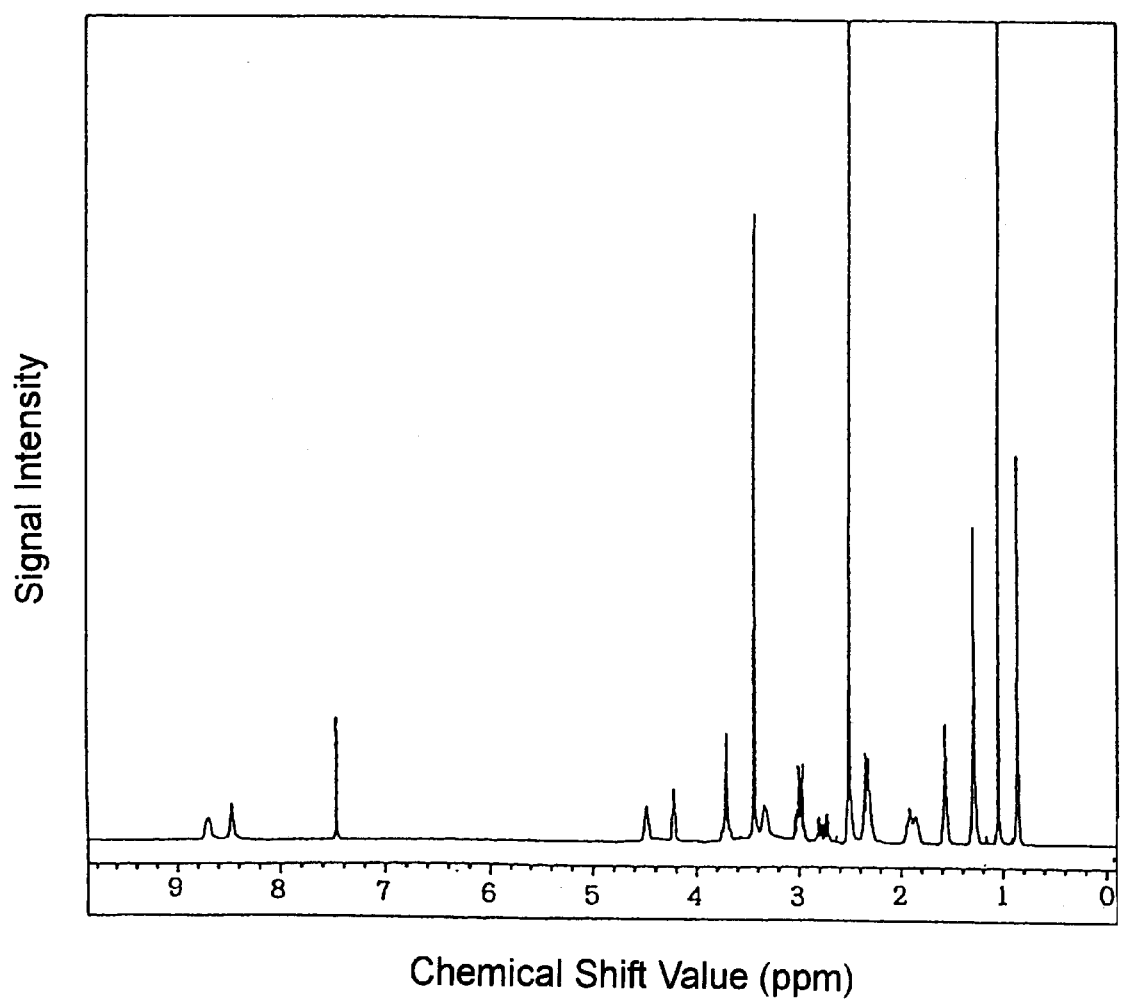
FIG. 1 illustrates the $^1$H-NMR spectrum of hexanoyl GM.

The present inventors have found that a compound of formula [I] below (hereinafter simply referred to as the compound of the present invention) is produced by reacting a compound of formula [II] with an SH group-containing compound and that the compound of the present invention has various strong physiological activities and is useful as a pharmaceutical compound for treating and/or preventing a diseases sensitive to the compound. Thus, the present invention has been completed.

The present invention is outlined as follows. The first invention of the present invention relates to a five-membered ring compound of formula [I]:

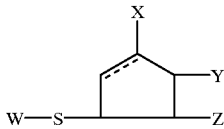

[I]

wherein the bond in the five-membered ring represented by a broken line means that the five-membered ring may be either a cyclopentene ring having a double bond or a saturated cyclopentane ring; if the five-membered ring is a cyclopentene ring, X is $OR_1$, Y is =O and Z is H; if the five-membered ring is a cyclopentane ring, X is =O, Y is $OR_2$ and Z is $OR_3$; $R_1$ is $R_4$ or —(CO)—$R_5$; $R_2$ is H, $R_6$ or —(CO)—$R_7$; and $R_3$ is H, $R_8$ or (CO)—$R_9$ (wherein $R_4$, $R_5$, $R_6$, $R_7$, $R_8$ and $R_9$ may be identical or different each other, and are an aliphatic group, an aromatic group or an aromatic aliphatic group, and $R_5$, $R_7$ and $R_9$ may be H), provided that $R_2$ and $R_3$ are not simultaneously H; and W is a residue in which an SH group is removed from an SH group-containing compound, or an optical isomer thereof, or a salt thereof.

The second invention of the present invention relates to a method for producing a five-membered ring compound of formula [I] or an optical isomer thereof, or a salt thereof, characterized in that the method comprises reacting an SH-group containing compound with a compound selected from the group consisting of a compound of formula [II]:

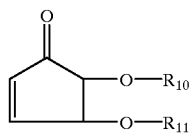

[II]

wherein $R_{10}$ is H, $R_{12}$ or —(CO)—$R_{13}$; $R_{11}$ is H, $R_{14}$ or —(CO)—$R_{15}$; (wherein $R_{12}$, $R_{13}$, $R_{14}$ and $R_{15}$ may be identical or different each other, and are an aliphatic group, an aromatic group or an aromatic aliphatic group, and $R_{13}$ and $R_{15}$ may be H), provided that $R_{10}$ and $R_{11}$ are not simultaneously H, or an optical isomer thereof, and a salt thereof.

The third invention of the present invention relates to a pharmaceutical composition, e.g., a carcinostatic composition or a composition for inducing apoptosis, which contains as an active ingredient at least one compound selected from the group consisting of the five-membered ring compound or an optical isomer thereof, and a salt thereof of the first invention of the present invention.

DETAILED DESCRIPTION OF THE INVENTION

The compound of formula [II] used in the present invention can be obtained, without limitation, according to a chemical synthesis method using 4,5-dihydroxy-2-cyclopenten-1-one of formula [III] (hereinafter simply referred to as cyclopentenone) below as a raw material, for example.

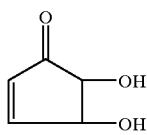

[III]

Cyclopentenones used in the present invention include isomers having hydroxyl groups at 4- and 5-positions configured in cis and isomers having the hydroxyl groups configured in trans. A cis or trans isomer of cyclopentenone or a mixture of the cis and trans isomers may be used in the present invention. Optical isomers thereof may also be used.

A cis isomer of cyclopentenone is obtained according to a chemical synthesis method [Helvetica Chimica Acta, 55:2838-2844 (1972)]. A trans isomer of cyclopentenone is obtained according to a chemical synthesis method [Carbohydrate Res., 247:217-222 (1993)] or by heating uronic acid (e.g., glucuronic acid), a uronic acid derivative (e.g., glucronolactone) or the like (see WO 98/13328).

For example, cyclopentenone is produced in a heat treatment product by heating a 1% solution of D-glucuronic acid as uronic acid at 121° C. for 4 hours. Cyclopentenone in the heat treatment product is extracted with a solvent. The extract is concentrated. The concentrate is then separated on silica gel column chromatography. Eluted fractions containing cyclopentenone are concentrated. Cyclopentenone is extracted from the concentrate with chloroform. The concentrated extract is the subjected to normal phase column chromatography, thereby isolating cyclopentenone in the heat treatment product.

Optical isomers, (−)-4,5-dihydroxy-2-cyclopenten-1-one and (+)-4,5-dihydroxy-2-cyclopenten-1-one, can be obtained by optically resolving the thus isolated cyclopentenone. Of course, synthesized cyclopentenone can be optically resolved.

For example, cyclopentenone is dissolved in ethanol. Hexane/ethanol (94/6) is further added to the solution in ethanol to prepare a cyclopentenone solution. Cyclopentenone can be optically resolved by subjecting this sample solution to HPLC, for example, under the following conditions: Chiralpack AS (Dicel Chemical Industries) column; column temperature: 40° C.; mobile phase: hexan/ethanol (94/6).

A compound of formula [IV]:

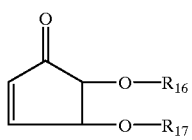

[IV]

wherein $R_{16}$ is H or —(CO)—$R_{18}$; $R_{17}$ is H or —(CO)—$R_{19}$; $R_{18}$ and $R_{19}$ may be identical or different each other, and are an aliphatic group, an aromatic group or an aromatic aliphatic group, provided that $R_{16}$ and $R_{17}$ are not simultaneously H, or an optical isomer thereof is produced in a reaction mixture by simultaneously or sequentially reacting cyclopentenone and/or an optical isomer thereof with a carboxylic acid having hydrogen, an aliphatic group, an aromatic group or an aromatic aliphatic group and/or a reactive derivative thereof.

The following carboxylic acids having hydrogen, an aliphatic group, an aromatic group or an aromatic aliphatic group and corresponding to $R_{18}$ and $R_{19}$ in the compound of formula [IV] are used in the present invention.

Formic acid can be used as a carboxylic acid having hydrogen.

A carboxylic acid having an alkyl group and a carboxylic acid having an alkenyl group can be used as a carboxylic acid having an aliphatic group.

A carboxylic acid having a linear or branched alkyl group can be used as a carboxylic acid having an alkyl group. Although the length of the alkyl chain can be suitably selected depending on the biological activity, solubility or the like of the compound of the present invention, a group of C1–30 is usually preferable.

Examples of carboxylic acids having linear alkyl groups which can be used include acetic acid, propionic acid, butyric acid, valeric acid, hexanoic acid, heptanoic acid, n-octanoic acid, pelargonic acid, n-decanoic acid, undecanoic acid, lauric acid, tridecanoic acid, myristic acid, pentadecanoic acid, palmitic acid, heptadecanoic acid, stearic acid, nonadecanoic acid, icosanoic acid, behenic acid, lignoceric acid, cerotic acid and melissic acid.

Examples of carboxylic acids having branched alkyl groups which can be used include isobutyric acid, isovaleric acid, 2-methylbutyric acid, pivalic acid, 4-methylvaleric acid and 1,2-dimethylvaleric acid.

A carboxylic acid having a linear or branched alkenyl group can be used as a carboxylic acid having an alkenyl group. Although the chain length, the degree of unsaturation and the position of unsaturated bond of the alkenyl group can be suitably selected depending on the biological activity, solubility or the like of the compound of the present invention, an alkenyl group of C2–30 is usually preferable.

Examples of carboxylic acids having linear alkenyl groups which can be used include acrylic acid, vinylacetic acid, crotonic acid, isocrotonic acid, allylacetic acid, 2-hexenoic acid, 3-hexenoic acid, 3-octenoic acid, obtusilic acid, 10-undecenoic acid, palmitoleic acid, petroselinic acid, elaidic acid, oleic acid, linoleic acid, α-linolenic acid, γ-linolenic acid, eleostearic acid, icosatrienoic acid, arachidonic acid, eicosapentaenoic acid, brassidic acid, erucic acid, docosahexaenoic acid, ximenic acid and 21-triacontenoic acid.

Examples of carboxylic acids having branched alkenyl groups which can be used include methacrylic acid, tiglic acid, angelic acid and α-ethylcrotonic acid.

A carboxylic acid having an alkyl group that has a lower alkoxyl group of C1–4 as a substituent such as methoxyacetic acid can be used as a carboxylic acid having a substituted aliphatic group. A carboxylic acid having an alkenyl group that has a lower alkoxycarbonyl of C2–5 as a substituent such as methylmaleic acid can be used.

Examples of carboxylic acids having aromatic groups which can be used include a carboxylic acid having a C6–11 aryl group such as benzoic acid, toluic acid, chlorobenzoic acid, bromobenzoic acid, nitrobenzoic acid, phthalic acid, isophthalic acid, terephthalic acid, salicylic acid, acetylsalicylic acid, acetylsalicylsalicylic acid, aminosalicylic acid, p-hydroxybenzoic acid, aminobenzoic acid, methoxybenzoic acid, acetamidobenzoic acid, vanillic acid, orsellinic acid, naphthoic acid, cinchomeronic acid, xanthurenic acid, quinic acid and kynureic acid. A carboxylic acid having an aromatic group used may be selected depending on the biological activity, solubility or the like of the compound of the present invention.

Examples of carboxylic acids having aromatic aliphatic groups which can be used include a carboxylic acid having a C1–30 alkyl C6–10 aryl group such as phenylacetic acid, phenylpropionic acid, phenyllactic acid, phenylpyruvic acid, cinnamic acid, atropic acid and naphthylacetic acid. A carboxylic acid having an aromatic aliphatic group used may be selected depending on the biological activity, solubility or the like of the compound of the present invention.

As used herein, examples of aliphatic groups include a linear or branched C1–30 alkyl group and a linear or branched C2–30 alkenyl group. Examples of aromatic groups include a C6–10 aryl group. Examples of aromatic aliphatic groups include a C1–30 alkyl C6–10 aryl group. These groups may have at least one substituent selected from the group consisting of functional groups including a C1–4 alkoxy group, a C2–5 alkoxycarbonyl group, a halogen (e.g., flourine, chlorine, bromine or iodine), an amino group, a hydroxyl group, a nitro group, an oxo group, a thiol group and a sulfate group.

Reactive derivatives of carboxylic acids are exemplified by an acid halide, an acid anhydride, an acid ester and a salt. A reactive derivative of the carboxylic acid to be used may be produced depending on the objects.

The reaction of a carboxylic acid and/or a reactive derivative thereof with cyclopentenone may be carried out such that $R_{16}$ and $R_{17}$ in the compound of formula [IV] become identical or different each other, or such that one of $R_{16}$ and $R_{17}$ remains to be an unreacted H. In other words, both of or one of the two hydroxyl groups in cyclopentenone may be reacted. Carboxylic acids having different groups for $R_{18}$, and $R_{19}$ and/or reactive derivatives thereof may be simultaneously reacted with cyclopentenone. Alternatively, they may be reacted sequentially. In the latter case, a compound in which $R_{18}$ and $R_{19}$ are different each other or in which only one of $R_{16}$ and $R_{17}$ is esterified can be efficiently produced by protecting one of the hydroxyl groups of cyclopentenone.

A compound of formula [V]:

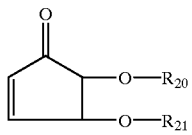

[V]

wherein $R_{20}$ and $R_{21}$ may be identical or different each other, and are hydrogen, an aliphatic group, an aromatic group or an aromatic aliphatic group, provided that $R_{20}$ and $R_{21}$ are not simultaneously H, or an optical isomer thereof is produced in a reaction mixture by simultaneously or sequentially reacting cyclopentenone and/or an optical isomer thereof with an alcohol having an aliphatic group, an aromatic group or an aromatic aliphatic group and/or a reactive derivative thereof.

The aliphatic groups, aromatic groups or aromatic aliphatic groups corresponding to $R_{20}$ and $R_{21}$ in the compound of formula [V] used in the present invention are as described above. Examples of alcohols having such groups include the following.

An alcohol having an alkyl group and an alcohol having an alkenyl groups can be used as an alcohol having an aliphatic group.

An alcohol having a linear or branched alkyl group can be used as an alcohol having an alkyl group. The chain length of the alkyl group can be suitably selected depending on the biological activity, solubility or the like of the compound of the present invention.

Examples of alcohols having linear alkyl groups which can be used include methanol, ethanol, propanol, butanol, pentanol, hexanol, heptanol, octanol, nonanol, decanol, lauryl alcohol, myristyl alcohol, palmityl alcohol and stearyl alcohol.

Examples of alcohols having branched alkyl groups which can be used include isobutyl alcohol, t-butyl alcohol, isoamyl alcohol and t-amyl alcohol.

An alcohol having a linear or branched alkenyl group can be used as an alcohol having an alkenyl group. The chain length, the degree of unsaturation and the position of unsaturated bond of the alkenyl group can be suitably selected depending on the biological activity, solubility or the like of the compound of the present invention.

Examples of alcohols having linear alkenyl groups which can be used include vinyl alcohol, allyl alcohol, crotonalcohol and 3-hexen-1-ol.

Examples of alcohols having branched alkenyl groups which can be used include geraniol, farnesol, geranylgeraniol, retinol, linalool, nerolidol and nerol.

Examples of alcohols having aromatic groups which can be used include phenol, cresol, nitrophenol, chlorophenol, bromophenol, catechol, resorcinol, hydroquinone and naphtol. An alcohol having an aromatic group to be used may be selected depending on the biological activity, solubility or the like of the compound of the present invention. The above-mentioned compound in which a hydroxyl group is directly attached to an aromatic group is classified in alcohols herein.

Alcohols having aromatic aliphatic groups which can be used include benzyl alcohol, phenethyl alcohol, phenacyl alcohol, styrene glycol and phenyl propanol. An alcohol having an aromatic aliphatic group to be used may be selected depending on the biological activity, solubility or the like of the compound of the present invention.

Reactive derivatives of alcohols are exemplified by an alkyl halide, an aryl halide, an acid ester, a diazo compound, a salt and an alkene, which is a dehydration product of an alcohol. A reactive derivative of the alcohol to be used may be produced depending on the objects.

The reaction of an alcohol and/or a reactive derivative thereof with cyclopentenone may be carried out such that $R_{20}$ and $R_{21}$ in the compound of formula [V] become identical or different each other, or such that one of $R_{20}$ and $R_{21}$ remains to be an unreacted H. In other words, both of or one of the two hydroxyl groups in cyclopentenone may be reacted. Alcohols having different groups for $R_{20}$ and $R_{21}$ and/or reactive derivatives thereof may be simultaneously reacted with cyclopentenone. Alternatively, they may be reacted sequentially. A compound in which $R_{20}$ and $R_{21}$ are different each other or a cyclopentenone derivative in which only one of $R_{20}$ and $R_{21}$ is etherified can be efficiently produced by protecting one of the hydroxyl groups of cyclopentenone.

Furthermore, a compound in which one of the hydroxyl groups of cyclopentenone is etherified and the other is esterified can be produced by simultaneously or sequentially reacting cyclopentenone with an alcohol and/or a reactive derivative thereof and a carboxylic acid and/or a reactive derivative thereof.

Known purification means including chemical means and physical means may be used for purification and isolation of the compound of formula [II] (e.g., the compound of formula [IV] or formula [V]) or an optical isomer thereof. Conventional purification means such as gel filtration, fractionation using a molecular weight fractionating membrane, solvent extraction, fractional distillation and various chromatographies using, for example, ion-exchange resins can be used in combination to purify and isolate the compound of formula [II] or an optical isomer thereof from the reaction product.

The compounds of formula [II] include isomers in which 4- and 5-positions are configured in cis and isomers in which 4- and 5-positions are configured in trans. A cis or trans isomer of the compound or a mixture of the isomers may be used in the present invention. Optical isomers thereof may also be used.

Salts of the compound of formula [II] or optical isomers thereof include, for example, pharmaceutically acceptable salts. Known methods can be used for the conversion.

The compound of the present invention is produced in a reaction mixture by reacting the compound of formula [II] or an optical isomer thereof, and/or a salt thereof with an SH group-containing compound.

For example, a compound of formula [VI] (hereinafter referred to as a cyclopentenone thio derivative):

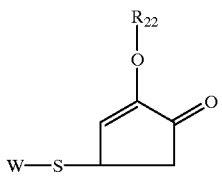

[VI]

wherein $R_{22}$ is $R_{23}$ or —(CO)—$R_{24}$; $R_{23}$ and $R_{24}$ are an aliphatic group, an aromatic group or an aromatic aliphatic group; $R_{24}$ may be hydrogen; and W is a residue in which an SH group is removed from an SH group-containing compound, is produced in a reaction mixture by reacting the compound of formula [II], an optical isomer thereof and/or a salt thereof with an SH group-containing compound such as an SH group-containing amino acid or a derivative thereof under acidic conditions.

Furthermore, a compound of formula [VII] (hereinafter referred to as a cyclopentanone thio derivative):

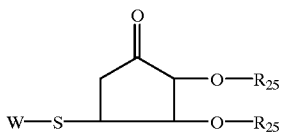

[VII]

wherein $R_{25}$ is H, $R_{27}$ or —(CO)—$R_{28}$; $R_{26}$ is H, $R_{29}$ or —(CO)—$R_{30}$; $R_{27}$, $R_{28}$, $R_{29}$ and $R_{30}$ may be identical or different each other, and are an aliphatic group, an aromatic group or an aromatic aliphatic group; $R_{28}$ and $R_{30}$ may be H, provided that $R_{25}$ and $R_{26}$ are not simultaneously H, is produced in a reaction mixture by reacting the compound of formula [II], an optical isomer thereof and/or a salt thereof with an SH group-containing compound such as an SH group-containing amino acid or a derivative thereof under neutral conditions.

Examples of the SH group-containing compounds include, but are not limited to, methanethiol, butanethiol, mercaptoethanol, SH group-containing amino acids and SH group-containing amino acid derivatives. Examples of the SH group-containing amino acids include cysteine and homocysteine.

The SH group-containing amino acid derivatives are exemplified by the derivatives of the above-mentioned amino acids such as cysteine derivatives, cysteine-containing peptides and cysteine derivative-containing peptides. The cysteine-containing peptide is not limited to specific one as long as the peptide has cysteine as its constituent. The cysteine-containing peptides of the present invention include small molecules such as oligopeptides (e.g., glutathione) and macromolecules such as proteins. Furthermore, peptides that contain cystine or homocystine can be used as cysteine- or homocysteine-containing peptides in the present invention by incorporating a treatment under conditions that generate cysteine- or homocysteine-containing peptides during the reaction, for example, under reductive conditions. The cysteine-containing peptides also include cysteine-containing peptides that contain a saccharide, a lipid or the like. Alternatively, the salts, acid anhydrides, esters or the like of the various substances as described above may be used.

As described above, the compound of the present invention is formed by reacting the compound of formula [II] and the SH group-containing compound.

Known purification means including chemical means and physical means may be used for purification and isolation of the compound of the present invention produced by reacting the compound of formula [II] or an optical isomer thereof, and/or a salt thereof with an SH group-containing compound such as an SH group-containing amino acid or a reactive derivative thereof, or an optical isomer thereof. Conventional purification means such as gel filtration, fractionation using a molecular weight fractionating membrane, solvent extraction, fractional distillation and various chromatographies using, for example, ion-exchange resins can be used in combination to purify and isolate the compound of the present invention or an optical isomer thereof, or a salt thereof from the reaction product.

Dihexanoylcyclopentenone which is produced, for example, by dissolving in cyclopentenone, n-hexanoic acid, dimethylaminopyridine and N,N'-dicyclohexylcarbodiimide in dichloromethane and reacting the mixture, can be purified on silica gel column chromatography.

A cyclopentenone thio derivative of formula [VIII]:

[VIII]

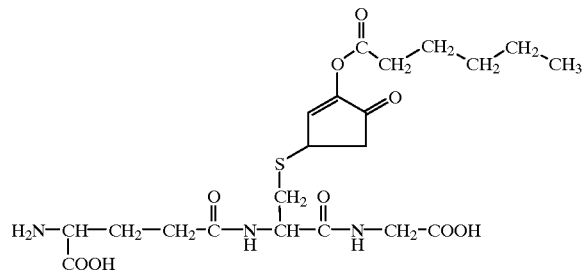

produced in a reaction mixture by reacting the compound of formula [II], an optical isomer thereof and/or a salt thereof with an SH group-containing compound such as an SH group-containing amino acid or a derivative thereof under neutral conditions.

Examples of the SH group-containing compounds include, but are not limited to, methanethiol, butanethiol, mercaptoethanol, SH group-containing amino acids and SH which is produced in a reaction mixture, for example, by reacting equivalent moles of dihexanoylcyclopentenone and glutathione (reduced) can be then purified and isolated by subjecting the reaction mixture containing the derivative to silica gel column chromatography.

Furthermore, 4,5-di-t-butylcyclopentenone ether, which is produced, for example, by dissolving cyclopentenone, t-butyl-2,2,2-trichloroacetimidate and boron trifluoride diethyl ether complex in dichloromethane and reacting the mixture, can be purified on thin-layer silica gel chromatography.

A cyclopentanone thio derivative of formula [IX]:

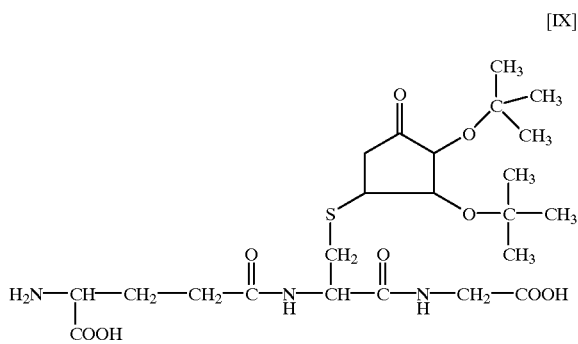

[IX]

which is produced in a reaction mixture, for example, by reacting 4,5-di-t-butylcyclopentenone ether and glutathione (reduced) can be then purified and isolated by subjecting the reaction mixture containing the derivative to silica gel column chromatography.

Optical isomers of the compound of the present invention can be separated by mechanical resolution of racemic mixture, preferential crystallization, resolution by crystallizing as a diastereomeric salt or an inclusion compound, kinetic resolution using an enzyme or a microorganism, chromatographic separation or the like.

Gas chromatography, liquid chromatography, thin-layer chromatography or the like using an appropriate chiral stationary phase can be used for chromatographic resolution.

A method in which a chiral stationary phase is used, a method in which a chiral eluent is used, separation as a diastereomer or the like can be used for optical resolution by liquid chromatography.

An amide-type stationary phase, a urea-type stationary phase, a ligand exchange-type stationary phase, a polysaccharide or polysaccharide derivative stationary phase, a protein stationary phase, a polymethacrylate ester stationary phase, a polymethacrylamide stationary phase or the like can be used as a chiral stationary phase.

A hexan-type eluent, an alcohol-type eluent, an aqueous (buffer) eluent or the like can be appropriately used as an eluent depending on the stationary phase used.

Salts of the compound of the present invention or optical isomers thereof include pharmaceutically acceptable salts. Known methods can be used for the conversion.

The compound of the present invention or an optical isomer thereof, or a salt thereof has physiological activities such as a carcinostatic activity, an antiproliferation activity against tumor cells and an apoptosis-inducing activity. Based on these activities, a pharmaceutical composition which contains at least one compound selected from the group consisting of the compound of the present invention or an optical isomer thereof, and a salt thereof as an active ingredient is useful, for example, as a pharmaceutical composition that acts against cancerous diseases such as a carcinostatic composition or a composition for preventing cancer. Thus, the pharmaceutical composition obtained according to the present invention is very useful as a pharmaceutical composition for diseases sensitive to the compound of the present invention or an optical isomer thereof, or a salt thereof such as a pharmaceutical composition for treating or preventing cancer.

The compound of the present invention or an optical isomer thereof, or a salt thereof has an antiproliferation activity or a carcinostatic activity against tumor cells such as human promyelocytic leukemia cell HL-60, human acute lymphoblastic leukemia cell MOLT-3, lung cancer cell A549, SV40-transformed lung cell WI-38VA13, hepatoma cell Hep G2, colonic adenocarcinoma cell HCT 116, human colonic adenocarcinoma cell SW480, human colonic adenocarcinoma cell WiDr, gastric adenocarcinoma cell AGS and a myeloma cell. In addition, these compounds have activities of inducing apoptosis in tumor cells. The mode of antiproliferative action against tumor cells of the compound of the present invention or an optical isomer thereof, or a salt thereof does not limit the present invention.

A carcinostatic composition can be produced by using at least one compound having a carcinostatic activity selected from the group consisting of the compound of the present invention or an optical isomer thereof, and a salt thereof as its active ingredient, and formulating it with a known pharmaceutical carrier. Generally, the carcinostatic composition of the present invention can be produced by mixing at least one compound selected from the group consisting of the compound of the present invention or an optical isomer thereof, and a salt thereof with a pharmaceutically acceptable liquid or solid carrier and, optionally, solvent, dispersing agent, emulsifier, buffering agent, stabilizer, excipient, binder, disintegrant, lubricant and the like to formulate it. The formulation may be in a form of a solid preparation such as tablet, granule, powder, epipastic and capsule, or a liquid preparation such as normal solution, suspension and emulsion. In addition, the composition may be formulated into a dried preparation, which can be reconstituted as a liquid preparation by adding an appropriate carrier before use.

The pharmaceutical carrier can be selected according to the above-mentioned particular administration route and dosage form. For an oral preparation, starch, lactose, sucrose, mannit, carboxymethylcellulose, cornstarch, inorganic salts and the like are utilized, for example. Binder, disintegrant, surfactant, lubricant, fluidity-promoting agent, tasting agent, coloring agent, flavoring agent and the like can also be included in oral preparations.

A parenteral preparation can be prepared according to conventional methods by dissolving or suspending the active ingredient of the present invention, i.e., at least one compound selected from the group consisting of the compound of the present invention or an optical isomer thereof, and a salt thereof, in a diluent. The diluents include injectable distilled water, physiological saline, aqueous glucose solution, injectable vegetable oil, sesame oil, peanut oil, soybean oil, corn oil, propylene glycol and polyethylene glycol. Optionally, sterilizer, stabilizer, osmotic regulator, smoothing agent and the like may be added to the solution or suspension.

The carcinostatic composition of the present invention is administered through a suitable route for the dosage form of the composition. The administration route is not limited to a specific one. The composition can be administered internally or externally (or topically) or by injection. The injectable preparation can be administrated intravenously, intramuscularly, subcutaneously, intradermally and the like, for example. External preparations include a suppository.

A dosage of the carcinostatic composition is appropriately determined and varies depending on the particular dosage form, administration route and purpose as well as age, weight and conditions of a patient to be treated. In general, a daily dosage for an adult person is 0.1 $\mu$g to 200 mg/kg in terms of the amount of a compound selected from the group consisting of the compound of the present invention or an optical isomer thereof, and a salt thereof contained in the formulation. Of course, the dosage can vary depending on various factors. Therefore, in some cases, a less dosage than the above may be sufficient but, in other cases, a dosage more than the above may be required. The pharmaceutical composition of the present invention can be administrated orally as it is, or it can be taken daily by adding to selected foods and drinks.

The composition for inducing apoptosis of the present invention can be formulated by using at least one compound having an apoptosis-inducing activity selected from the group consisting of the compound of the present invention or an optical isomer thereof, and a salt thereof as its active ingredient according to the same manner as that described above with respect to the carcinostatic composition. They can be administered according to the same manner as that described above with respect to the carcinostatic composition.

A dosage of the composition for inducing apoptosis is appropriately determined according to the same manner as described above with respect to the carcinostatic composition. In general, a daily dosage for an adult person is 0.1 µg to 100 mg/kg in terms of the amount of a compound selected from the group consisting of the compound of the present invention or an optical isomer thereof, and a salt thereof contained in the formulation. Of course, the dosage can vary depending on various factors. Therefore, in some cases, a less dosage than the above may be sufficient but, in other cases, a dosage more than the above may be required. The pharmaceutical composition of the present invention can be administrated orally as it is, or it can be taken daily by adding to selected foods and drinks.

The apoptosis is considered to be a death that has been originally programmed in the genome of a cell, and is different from necrosis, which is a pathological cell death. Specifically, it is considered that the following processes lead to the death. The activation of a gene that programs the apoptosis triggered by certain external or internal factor(s) causes the biosynthesis of a programmed death protein on the basis of the gene. The thus generated programmed death protein destroys the cell. The composition for inducing apoptosis of the present invention can induce the apoptosis in desired tissues or cells and is very useful because it makes it possible to eliminate unnecessary or pathogenic cells from a living body in a natural manner.

The composition for inducing apoptosis of the present invention can be used in a method for inducing apoptosis. Specifically, at least one compound selected from the group consisting of the compound of the present invention or an optical isomer thereof, and a salt thereof can be used as an active ingredient to induce apoptosis. The method is useful for elucidating the mechanism of induction of apoptosis, as well as screening for inducers of apoptosis and inhibitors of apoptosis induction.

The compound of the present invention or an optical isomer thereof, or a salt thereof has physiological activities such as a carcinostatic activity, an antiproliferation activity against tumor cells and an apoptosis-inducing activity. Based on these activities, a food or a drink which contains at least one compound selected from the group consisting of the compound of the present invention or an optical isomer thereof, and a salt thereof is useful as a functional food or drink having the above-mentioned various physiological activities.

The compound of the present invention can also be used in the production of the food or drink of the present invention, which compound is produced during the production process in which the compound of general formula [II] and an SH group-containing compound are used.

The functional foods or drinks include a food or a drink which contains, which is produced by diluting, and/or which is produced by adding thereto at least one compound selected from the group consisting of the compound of the present invention or an optical isomer thereof, and a salt thereof.

The process for producing the functional food or drink is not limited to a specific one. Any processes including cooking, processing and other generally employed processes for producing a food or a drink can be used as long as the resultant food or drink contains an effective amount of at least one compound having a physiological activity selected from the group consisting of the compound of the present invention or an optical isomer thereof, and a salt thereof.

The forms of the functional foods or drinks include, but are not limited to, any edible forms including tablet, granule, capsule, gel, sol and the like as long as they contain, are produced by adding thereto, and/or are produced by diluting at least one compound having physiological functions such as a carcinostatic activity or an apoptosis-inducing activity selected from the group consisting of the compound of the present invention or an optical isomer thereof, and a salt thereof.

The functional foods or drinks contain the compound of the present invention or an optical isomer thereof, or a salt thereof which has physiological activities. Based on the various physiological activities of the compounds such as a carcinostatic activity and an apoptosis-inducing activity, these functional foods or drinks serve as healthy foods or drinks that have an effect of preventing carcinogenesis, an effect of suppressing cancer or the like when they are taken. Thus, they are useful for maintaining homeostasis in a living body, particularly, for keeping gastrointestinal health.

No toxicity is observed when a physiologically effective amount of the compound of the present invention or an optical isomer thereof, or a salt thereof is administered. For example, no death was observed when either one of the compound of formula [VIII] or the compound of formula [IX] or optical isomers thereof, or salts thereof was orally administered to a rat at a single dosage of 1000 mg/kg.

As described above, the compound of the present invention or an optical isomer thereof, or a salt thereof are very useful in a wide variety of fields including medicine, foods and drinks based on their various physiological functions. The compound of the present invention is also produced as a product of reaction between the compound of formula [II] and an SH group-containing compound (e.g., an SH group-containing amino acid) or a derivative thereof (e.g., a cysteine-containing peptide) in a food or a drink. Use of such artificially produced compound is also encompassed by the present invention.

Cyclopentenone and 2-hydroxy-4-glutathion-S-yl-2-cyclopenten-1-one (a product of reaction between cyclopentenone and an SH group-containing compound) have effects of treating viral infections. Thus, there is provided an antiviral composition containing cyclopentenone and/or 2-hydroxy-4-glutathion-S-yl-2-cyclopenten-1-one as an active ingredient.

The antiviral composition can be formulated by using at least one compound selected from the group consisting of cyclopentenone or an optical isomer thereof, and a salt thereof as well as 2-hydroxy-4-glutathion-S-yl-2-cyclopenten-1-one or an optical isomer thereof, and a salt thereof as its active ingredient according to the same manner as that described above with respect to the carcinostatic composition. They can be administered according to the same manner as that described above with respect to the carcinostatic composition.

A dosage of the antiviral composition is appropriately determined according to the same manner as described above with respect to the carcinostatic composition. In general, a daily dosage for an adult person is 0.1 µg to 100 mg/kg in terms of the amount of the compound contained in the formulation. Of course, the dosage can vary depending on various factors. Therefore, in some cases, a less dosage than the above may be sufficient but, in other cases, a dosage more than the above may be required.

An antiviral pesticide, an antiviral feed and antiviral composition for soaking an organism can be produced by using a compound selected from these compounds used in the antiviral composition as an active ingredient.

No death was observed when cyclopentenone was orally administered to a mouse at a single dosage of 100 mg/kg. Also, no death was observed when 2-hydroxy-4-glutathion-S-yl-2-cyclopenten-1-one was orally administered to a rat at a single dosage of 1000 mg/kg.

As described above, cyclopentenone and 2-hydroxy-4-glutathion-S-yl-2-cyclopenten-1-one are useful as antiviral compounds.

The following examples further illustrate the present invention in detail but are not to be construed to limit the scope thereof. Percent (%) in Examples means percent by weight.

REFERENTIAL EXAMPLE 1

(1) 10 g of D-glucuronic acid (Sigma, G 5269) was dissolved in 1 liter of water. The solution was heated at 121° C. for 4 hours and then concentrated to a volume of about 10 ml under reduced pressure. 40 ml of an upper layer of a mixture of butyl acetate:acetic acid:water=3:2:2 was added thereto and mixed. A supernatant obtained by centrifuging the mixture was concentrated under reduced pressure to a volume of about 10 ml.

The extract was applied to silica gel BW-300SP for column chromatography (2×28 cm, Fuji Sylysia). Separation was carried out using an upper layer of butyl acetate:acetic acid:water=3:2:2 as an eluent, at a pressure of 0.2 kg/cm² using a compressor and at a flow rate of 5 ml/min. Each fraction contained 10 ml of the fractionated eluate. A portion of each fraction was analyzed on thin-layer chromatography. As a result, 61st to 80th fractions contained cyclopentenone with high purity. These fractions were collected and concentrated under reduced pressure. The concentrate was extracted with 40 ml of chloroform. The extract was concentrated under reduced pressure to obtain 100 mg of cyclopentenone.

The preparation was separated on normal phase HPLC using Palpack Type S column (Takara Shuzo) and detected on the basis of ultraviolet absorbance at 215 nm. This procedure confirmed that the preparation had a purity of 98%.

(2) 113.9 mg of cyclopentenone obtained according to the method as described in Referential Example 1-(1) was dissolved in 2.85 ml of ethanol. 3.85 ml of hexane/ethanol (94/6) was further added to the solution in ethanol to prepare 17 mg/ml cyclopentenone solution. This solution was filtrated through a 0.5-µm filter to obtain a sample solution for optical resolution HPLC.

The sample solution was subjected to optical resolution HPLC under the conditions as described below. Fractions containing a (−) isomer and a (+) isomer of cyclopentenone were separately collected from the former peak and the latter peak, respectively. The fractions were evaporated to dryness under reduced pressure to obtain 43.2 mg of the (−) isomer and 43.0 mg of and the (+) isomer of cyclopentenone.

Conditions for Optical Resolution HPLC

Column: Chiralpack AS (Dicel Chemical Industries, 2.0 cm×25.0 cm);

Column temperature: 40° C.;

Mobile phase: hexan/ethanol (94/6);

Flow rate: 14.0 ml/min.;

Detection: UV 210 nm;

Amount of sample injected: 150 µl (2.55 mg).

Since both of the resulting (−) isomer and (+) isomer of cyclopentenone contained an enantiomer at a concentration of about 1%, they were optically resolved again under the above-mentioned conditions. As a result, 19.7 mg of the (−) isomer of cyclopentenone free of an enantiomer was obtained from 30.0 mg of the (−) isomer from the former peak. 27.7 mg of the (+) isomer of cyclopentenone free of an enantiomer was obtained from 37.4 mg of the (+) isomer from the latter peak. The elution time in the optical resolution HPLC for the (−) isomer of cyclopentenone was 33 min. and that for the (+) isomer was 40 min.

(3) 1 ml of anhydrous pyridine (Nacalai Tesque, 295-26) and 0.1 ml of acetic anhydride (Nacalai Tesque, 002-26) were added to 29.6 mg of cyclopentenone obtained as described in Referential Example 1-(1). The mixture was stirred at room temperature for 3 hours. The reaction mixture was extracted with chloroform to obtain 36 mg of diacetylcyclopentenone.

Mass spectrometric analysis of the resulting diacetylcyclopentenone was carried out using DX302 mass spectrometer (Nippon Denshi). Additionally, diacetylcyclopentenone was dissolved in $CDCl_3$ and subjected to structural analysis by NMR using a nuclear magnetic resonance apparatus JNM-A500 (Nippon Denshi). The results are shown below. The chemical shift values in $^1$H-NMR are expressed assuming the chemical shift value of chloroform as 7.24 ppm.

MS m/z 199 (M+H)$^+$; $^1$H-NMR; δ2.12 (3H, S. —OCOCH$_3$), 2.16 (3H, S, —OCOCH$_3$), 5.16 (1H, d, J=3.0 Hz, H-5), 5.89 (1H, m, H-4), 6.40 (1H, d-d, J=1.5, 6.5 Hz, H-2), 7.43 (1H, d-d, J=2.5, 6.5 Hz, H-3).

(4) 15.9 mg of the (−) isomer of cyclopentenone obtained as described in Referential Example 1-(2) was used to carry out the reaction as described in Referential Example 1-(3) to obtain 15.1 mg of a diacetyl (−) isomer of cyclopentenone. Similar results with those in Referential Example 1-(3) were obtained when the isomer was subjected to structural analysis by mass spectrometry and nuclear magnetic resonance as described in Referential Example 1-(3).

(5) 16.7 mg of the (+) isomer of cyclopentenone obtained as described in Referential Example 1-(2) was used to carry out the reaction as described in Referential Example 1-(3) to obtain 18.8 mg of a diacetyl (+) isomer of cyclopentenone. Similar results with those in Referential Example 1-(3) were obtained when the isomer was subjected to structural analysis by mass spectrometry and nuclear magnetic resonance as described in Referential Example 1-(3).

(6) 44.3 mg of benzoic acid (Nacalai Tesque, 041-20), 7.5 mg of dimethylaminopyridine (DMAP; Tokyo Kasei Kogyo, D1450), 51.0 mg of N,N'-dicyclohexylcarbodiimide (DCC: Peptide Institute, 1001) and 5 ml of chloroform were added to 13.8 mg of cyclopentenone. The mixture was stirred on ice for 4 hours. A filtrate obtained by the filtration of the reaction mixture was applied to silica gel column (75 ml) and eluted with chloroform to obtain fractions containing dibenzoylcyclopentenone. The solvent in the fractions was removed under reduced pressure, the residue was dissolved in ethanol, and the solution was separated on silica gel thin-layer chromatography using a 99:1 mixture of chloroform and methanol as a developing solvent. Silica gel at Rf=0.45–0.55 was scraped from the thin layer and extracted with chloroform to obtain 3.2 mg of dibenzoylcyclopentenone.

Structural analysis by mass spectrometry and nuclear magnetic resonance of the thus obtained dibenzoylcyclopentenone was carried out as described in Referential Example 1-(3). The results are shown below.

MS m/z 323 (M+H)$^+$; $^1$H-NMR; δ5.56 (1H, d, J=3.0 Hz, H-5), 6.30 (1H, m, H-4), 6.54 (1H, d-d, J=1.5, 6.5 Hz, H-2), 7.44 (4H, m, H of aromatic ring), 7.58 (2H, m, H of aromatic ring), 7.64 (1H, d-d, J=2.0, 6.5 Hz, H-3), 8.06 (4H, m, H of aromatic ring).

(7) 22.1 mg of the (−) isomer of cyclopentenone, 71.9 mg of benzoic acid, 12.1 mg of DMAP and 80.3 mg of DCC were used to carry out the reaction as described in Referential Example 1-(6) to obtain 19.2 mg of a dibenzoyl (−) isomer of cyclopentenone. Similar results with those in Referential Example 1-(6) were obtained when the isomer was subjected to structural analysis by mass spectrometry and nuclear magnetic resonance as described in Referential Example 1-(6).

(8) 20.4 mg of the (+) isomer of cyclopentenone, 65.6 mg of benzoic acid, 11.0 mg of DMAP and 74.3 mg of DCC were used to carry out the reaction as described in Referential Example 1-(6) to obtain 21.4 mg of a dibenzoyl (+) isomer of cyclopentenone. Similar results with those in Referential Example 1-(6) were obtained when the isomer was subjected to structural analysis by mass spectrometry and nuclear magnetic resonance as described in Referential Example 1-(6).

(9) 30 mg of cyclopentenone, 10 mg of DMAP and 153 mg of hexanoic acid (Nacalai Tesque, 070-26) were dissolved in 5.9 ml of dichloromethane. 108 mg of DCC was added thereto while cooling on ice. After reacting for 1 hour, the reaction mixture was separated and purified on silica gel thin-layer chromatography using chloroform as a developing solvent. Silica gel at Rf=0.3–0.4 was scraped from the thin layer and extracted with chloroform to obtain 11 mg of dihexanoylcyclopentenone.

The thus obtained dihexanoylcyclopentenone was dissolved in $CDCl_3$ for confirmation by nuclear magnetic resonance (NMR) using a nuclear magnetic resonance apparatus JNM-EX270 FT NMR system (Nippon Denshi). The chemical shift values in $^1$H-NMR are expressed assuming the chemical shift value of tetramethylsilane as 0 ppm.

The results are shown below.

$^1$H-NMR; δ7.44 (1H, dd, $J_{2-3}$=6.27 Hz, $J_{3-4}$=1.98 Hz, H-3), 6.42 (1H, dd, $J_{2-3}$=6.27 Hz, $J_{3-4}$=1.32 Hz, H-2), 5.91 (1H, m, H-4), 5.16 (1H, d, $J_{4-5}$=2.97 Hz, H-5), 2.42 (2H, t, J=7.26 Hz), 2.38 (2H, t, J=7.76 Hz), 1.65 (4H, m), 1.26 (8H, m), 0.88 (6H, t).

(10) 30 mg of cyclopentenone, 10 mg of DMAP and 301 mg of myristic acid (Tokyo Kasei Kogyo, M0476) were dissolved in 5.9 ml of dichloromethane. 108 mg of DCC was added thereto while cooling on ice. After reacting for 1 hour, the reaction mixture was separated on silica gel thin-layer chromatography using chloroform as a developing solvent. Silica gel at Rf=0.45–0.55 was scraped from the thin layer and extracted with chloroform to obtain 53 mg of dimyristoylcyclopentenone.

Structural analysis by nuclear magnetic resonance of the thus obtained dimyristoylcyclopentenone was carried out as described in Referential Example 1-(9). The results are shown below.

$^1$H-NMR; δ7.45 (1H, dd, $J_{2-3}$=5.94 Hz, $J_{3-4}$=2.31 Hz, H-3), 6.42 (1H, dd, $J_{2-3}$=5.31 Hz, $J_{3-4}$=1.32 Hz, H-2), 5.92 (1H, m, H-4), 5.16 (1H, d, $J_{4-5}$=2.64 Hz, H-5), 2.42 (2H, t, J=7.26 Hz), 2.38 (2H, t, J=7.91 Hz), 1.63 (4H, m), 1.26 (32H, m), 0.88 (6H, t).

(11) 30 mg of cyclopentenone, 10 mg of DMAP and 190 mg of octanoic acid (Nacalai Tesque, 071-11) were dissolved in 5.9 ml of dichloromethane. 108 mg of DCC was added thereto while cooling on ice. After reacting for 1 hour, the reaction mixture was separated on silica gel thin-layer chromatography using chloroform as a developing solvent. Silica gel at Rf=0.25–0.35 was scraped from the thin layer and extracted with chloroform to obtain 27 mg of dioctanoylcyclopentenone.

Structural analysis by nuclear magnetic resonance of the thus obtained dioctanoylcyclopentenone was carried out as described in Referential Example 1-(9). The results are shown below.

$^1$H-NMR; δ7.44 (1H, dd, $J_{2-3}$=6.1 Hz, $J_{3-4}$=2.16 Hz, H-3), 6.41 (1H, dd, $J_{2-3}$=6.1 Hz, $J_{3-4}$=1.48 Hz, H-2), 5.92 (1H, m, H-4), 5.16 (1H, d, $J_{4-5}$=2.97 Hz, H-5), 2.42 (2H, t, J=7.59 Hz), 2.38 (2H, t, J=7.91 Hz), 1.65 (4H, m), 1.29 (16H, m), 0.88 (6H, t).

(12) 30 mg of cyclopentenone, 10 mg of DMAP and 190 mg of 3-octenoic acid (Tokyo Kasei Kogyo, 00070) were dissolved in 5.9 ml of dichloromethane. 108 mg of DCC was added thereto while cooling on ice. After reacting for 1 hour, the reaction mixture was separated on silica gel thin-layer chromatography using chloroform as a developing solvent. Silica gel at Rf=0.25–0.35 was scraped from the thin layer and extracted with chloroform to obtain 25 mg of di-3-octenoylcyclopentenone.

Structural analysis by nuclear magnetic resonance of the thus obtained di-3-octenoylcyclopentenone was carried out as described in Referential Example 1-(9). The results are shown below.

$^1$H-NMR; δ7.44 (1H, dd, $J_{2-3}$=6.27 Hz, $J_{3-4}$=2.32 Hz, H-3), 6.42 (1H, dd, $J_{2-3}$=6.27 Hz, $J_{3-4}$=1.49 Hz, H-2), 5.91 (1H, m, H-4), 5.55 (4H, m), 5.16 (1H, d, $J_{4-5}$=2.97 Hz, H-5), 3.12 (4H, dd, J=12.85 Hz, J=6.59 Hz), 2.04 (4H, m), 1.33 (8H, m), 0.89 (6H, t).

(13) 30 mg of cyclopentenone, 10 mg of DMAP and 115 mg of n-butyric acid (Tokyo Kasei Kogyo, B0754) were dissolved in 5.9 ml of dichloromethane. 108 mg of DCC was added thereto while cooling on ice. After reacting for 1 hour, the reaction mixture was separated on silica gel thin-layer chromatography using chloroform as a developing solvent. Silica gel at Rf=0.20–0.30 was scraped from the thin layer and extracted with chloroform to obtain 16 mg of dibutyrylcyclopentenone.

Structural analysis by nuclear magnetic resonance of the thus obtained dibutyrylcyclopentenone was carried out as described in Referential Example 1-(9). The results are shown below.

$^1$H-NMR; δ7.45 (1H, dd, $J_{2-3}$=6.27 Hz, $J_{3-4}$=2.13 Hz, H-3), 6.42 (1H, dd, $J_{2-3}$=6.27 Hz, $J_{3-4}$=1.65 Hz, H-2), 5.91 (1H, m, H-4), 5.16 (1H, d, $J_{4-5}$=2.64 Hz, H-5).

(14) 30 mg of cyclopentenone, 10 mg of DMAP and 226 mg of n-decanoic acid (Tokyo Kasei Kogyo, D0017) were dissolved in 5.9 ml of dichloromethane. 108 mg of DCC was added thereto while cooling on ice. After reacting for 1 hour, the reaction mixture was separated on silica gel thin-layer chromatography using chloroform as a developing solvent. Silica gel at Rf=0.35–0.45 was scraped from the thin layer and extracted with chloroform to obtain 35 mg of didecanoylcyclopentenone.

Structural analysis by nuclear magnetic resonance of the thus obtained didecanoylcyclopentenone was carried out as described in Referential Example 1-(9). The results are shown below.

¹H-NMR; δ7.44 (1H, dd, $J_{2-3}$=6.27 Hz, $J_{3-4}$=1.97 Hz, H-3), 6.42 (1H, dd, $J_{2-3}$=6.27 Hz, $J_{3-4}$=1.3 Hz, H-2), 5.91 (1H, m, H-4), 5.15 (1H, d, $J_{4-5}$=2.97 Hz, H-5), 2.42 (2H, t, J=7.24 Hz), 2.38 (2H, t, J=7.91 Hz), 1.65 (4H, m), 1.26 (24H, m), 0.88 (6H, t).

(15) 30 mg of cyclopentenone, 16 mg of DMAP, 66 mg of triethylamine (Tokyo Kasei Kogyo, T0424) and 122 mg of n-valeric anhydride (Tokyo Kasei Kogyo, V0006) were dissolved in 5.9 ml of dichloromethane. The mixture was reacted on ice for 1 hour. The reaction mixture was developed on silica gel thin-layer chromatography using chloroform:methanol=200:1 as a developing solvent. Silica gel at Rf=0.7–0.8 was scraped from the thin layer and extracted with chloroform to obtain 39 mg of divalerylcyclopentenone.

Structural analysis by nuclear magnetic resonance of the thus obtained divalerylcyclopentenone was carried out as described in Referential Example 1-(9). The results are shown below.

¹H-NMR; δ7.45 (1H, dd, J2-3=6.11 Hz, J3-4=1.66 Hz, H-3), 6.42 (1H, dd, J2-3=6.11 Hz, J3-4=1.66 Hz, H-2), 5.91 (1H, m, H-4), 5.16 (1H, d, J4-5=2.97 Hz, H-5), 2.43 (2H, dd, J=7.59, 7.59 Hz), 2.39 (2H, dd, J=7.59, 7.59 Hz), 1.65 (4H, m), 1.38 (4H, m), 0.93 (6H, dd, J=7.26, 7.26 Hz).

(16) 30 mg of cyclopentenone, 16 mg of DMAP, 66 mg of triethylamine and 86 mg of propionic anhydride (Tokyo Kasei Kogyo, P0513) were dissolved in 5.9 ml of dichloromethane. The mixture was reacted on ice for 1 hour. The reaction mixture was developed on silica gel thin-layer chromatography using chloroform:methanol=200:1 as a developing solvent. Silica gel at Rf=0.5–0.6 was scraped from the thin layer and extracted with chloroform to obtain 31 mg. of dipropionylcyclopentenone.

Structural analysis by nuclear magnetic resonance of the thus obtained dipropionylcyclopentenone was carried out as described in Referential Example 1-(9). The results are shown below.

¹H-NMR; δ7.45 (1H, dd, J2-3=6.27 Hz, J3-4=2.15 Hz, H-3), 6.42 (1H, dd, J2-3=6.27 Hz, J3-4=1.49 Hz, H-2), 5.91 (1H, m, H-4), 5.16 (1H, d, J4-5=2.97 Hz, H-5), 2.46 (2H, dd, J=15.01, 7.59 Hz), 2.42 (2H, dd, J=15.01, 7.59 Hz), 1.18 (6H, dd, J=7.59, 7.59 Hz).

(17) 2 g of cyclopentenone, 733 mg of DMAP, 4.1 ml of trans-2-hexenoic acid (Tokyo Kasei Kogyo, H0383) and 5.57 g of DCC were dissolved in 200 ml of dichloromethane. The mixture was reacted at room temperature for 2 hours. The reaction mixture was subjected to silica gel column chromatography using hexane:ethyl acetate=8:1 as a solvent to obtain a fraction that results in a single spot on silica gel thin-layer chromatography. The fraction was concentrated under reduced pressure to obtain about 900 mg of oil of di-2-hexenoylcyclopentenone.

Structural analysis by nuclear magnetic resonance of the thus obtained di-2-hexenoylcyclopentenone was carried out as described in Referential Example 1-(9). The results are shown below.

¹H-NMR; δ0.92 (6H, m, 11-H+11'-H), 1.48 (4H, m, 10-H+10'-H), 2.18 (4H, m, 9-H, 9'-H), 5.22 (1H, d, J=3.0 Hz, 5-H), 5.85 (2H, m, 7-H+7'-H), 5.98 (1H, m, 4-H), 6.41 (1H, dd, J=1.0, 6.0 Hz, 2-H), 7.04 (2H, m, 8-H+8'-H), 7.47 (1H, dd, J=2.0, 6.0 Hz, 3-H).

The positions of carbons in the 2-hexenoyl group attached at 5-position of cyclopentenone were defined as 6-position to 11-position starting from the carbonyl group. The positions of carbons in the 2-hexenoyl group attached at 4-position of cyclopentenone were defined as 6'-position to 11'-position starting from the carbonyl group.

(18) 1.2 g of cyclopentenone was dissolved in 200 ml of dichloromethane. 1.7 ml of isobutyric anhydride (Nacalai Tesque), 427 mg of DMAP and 1.46 ml of triethylamine (Nacalai Tesque) were added thereto. The mixture was reacted at room temperature for 1 hour and concentrated under reduced pressure. The residue was dissolved in ethyl acetate and washed with 10% citric acid and saturated aqueous sodium hydrogencarbonate solution. The solution was concentrated under reduced pressure. The concentrate was separated on silica gel column chromatography using hexane:ethyl acetate=8:1 as a developing solvent to obtain a fraction that results in a spot at Rf=0.2 on silica gel thin-layer chromatography using hexane:ethyl acetate=6:1 as a developing solvent. The solvent in the fraction was removed by evaporating under reduced pressure to obtain 470 mg of oil containing diisobutyrylcyclopentenone with high purity.

Structural analysis by nuclear magnetic resonance of the thus obtained diisobutyrylcyclopentenone dissolved in heavy chloroform was carried out as described in Referential Example 1-(3). The results are shown below.

¹H-NMR; δ1.18 (12H, m, 7-H, 8-H, 10-H, 11-H), 2.61 (2H, m, 6-H, 9-H), 5.10 (1H, d, J=3.0 Hz, 5-H), 5.88 (1H, m, 4-H), 6.39 (1H, dd, J=1.5, 6.0 Hz, 2-H), 7.41 (1H, dd, J=2.5, 6.0 Hz, 3-H).

The results are expressed assuming the chemical shift value of the residual proton of heavy chloroform as 7.24 ppm.

(19) 1.5 g of cyclopentenone was dissolved in 200 ml of dichloromethane. 2.7 g of methoxyacetic acid (Nacalai Tesque), 794 mg of DMAP and 5.36 g of DCC (Nacalai Tesque) were added thereto. The mixture was reacted at room temperature for 2 hours and concentrated under reduced pressure. The residue was dissolved in ethyl acetate and washed with 10% citric acid and saturated aqueous sodium hydrogencarbonate solution. The solution was concentrated under reduced pressure. The concentrate was separated on silica gel column chromatography using hexane ethyl acetate=2:3 as a developing solvent to obtain a fraction that results in a spot at Rf=0.34 on silica gel thin-layer chromatography using hexane:ethyl acetate=1:1 as a developing solvent. The solvent in the fraction was removed by evaporating under reduced pressure to obtain 300 mg of oil containing dimethoxyacetylcyclopentenone with high purity.

Structural analysis by nuclear magnetic resonance of the thus obtained dimethoxyacetylcyclopentenone dissolved in heavy chloroform was carried out as described in Referential Example 1-(3). The results are shown below.

¹H-NMR; δ3.45 (6H, s, 7-H, 9-H), 4.13 (4H, m, 6-H, 8-H), 5.30 (1H, d, J=3.0 Hz, 5-H), 5.99 (1H, m, 4-H), 6.44 (1H, dd, J=1.5, 6.5 Hz, 2-H), 7.46 (1H, dd, J=2.0, 6.5 Hz, 3-H).

The results are expressed assuming the chemical shift value of the residual proton of heavy chloroform as 7.24 ppm.

(20) 1.1 g of cyclopentenone was dissolved in 200 ml of dichloromethane. 3.4 g of methylmaleic acid, 610 mg of DMAP and 4.12 g of DCC were added thereto. The mixture was reacted at room temperature for 2 hours and concentrated under reduced pressure. The residue was dissolved in ethyl acetate and washed with 10% citric acid and saturated aqueous sodium hydrogencarbonate solution. The solution was concentrated under reduced pressure. The concentrate was separated on silica gel column chromatography using hexane:ethyl acetate=3:2 as a developing solvent to obtain a fraction that results in a spot at Rf=0.6 and a fraction that results in a spot at Rf=0.45 on silica gel thin-layer chromatography using hexane:ethyl acetate=1:1 as a developing solvent.

The solvent in the fractions was removed by evaporating under reduced pressure to obtain 300 mg of solid containing dimethylfumarylcyclopentenone with high purity from the Rf=0.6 fraction and 300 mg of oil containing dimethylmaleylcyclopentenone with high purity from the Rf=0.45 fraction.

Structural analysis by nuclear magnetic resonance of the products dissolved in heavy chloroform was carried out as described in Referential Example 1-(3). The results are shown below.

$^1$H-NMR; Dimethylfumarylcyclopentenone; δ3.80 (6H, s, 10-H, 15-H), 5.31 (1H, d, J=3.0 Hz, 5-H), 6.03 (1H, m, 4-H), 6.48 (1H, dd, J=1.0, 6.0 Hz, 2-H), 6.90 (4H, m, 7-H, 8-H, 12-H, 13-H), 7.50 (1H, dd, J=2.0, 6.0 Hz, 3-H). Dimethylmaleylcyclopentenone; δ3.76 (6H, s, 10-H, 15-H), 5.31 (1H, d, J=3.0 Hz, 5-H), 6.07 (1H, m, 4-H), 6.31 (4H, m, 7-H, 8-H, 12-H, 13-H), 6.44 (1H, dd, J=1.5, 6.0 Hz, 2-H), 7.58 (1H, dd, J=2.0, 6.0 Hz, 3-H).

The results are expressed assuming the chemical shift value of the residual proton of heavy chloroform as 7.24 ppm.

(21) 44 mg of cyclopentenone and 492 mg of benzyl 2,2,2-trichloroacetimidate (Aldrich, 14,033-3) was dissolved in 2.5 ml of dichloromethane (Wako Pure Chemical Industries, 135-02441) under argon flow. 1 ml of 28 μl/ml boron trifluoride diethyl ether complex (Wako Pure Chemical Industries, 022-08362) solution in dichloromethane was slowly added thereto while stirring. After stirring for 8 hours at room temperature, the mixture was concentrated under reduced pressure. The concentrate was subjected to silica gel thin-layer chromatography using chloroform:methanol=19:1 as a developing solvent to purify 4-benzylcyclopentenone ether, 5-benzylcyclopentenone ether and 4,5-dibenzylcyclopentenone ether. The Rf values for 4-benzylcyclopentenone ether, 5-benzylcyclopentenone ether and 4,5-dibenzylcyclopentenone ether were 0.3, 0.45 and 0.8, respectively. The yields of 4-benzylcyclopentenone ether, 5-benzylcyclopentenone ether and 4,5-dibenzylcyclopentenone ether were 3.7%, 3.7% and 2.5%, respectively.

Structures of 4-benzylcyclopentenone ether, 5-benzylcyclopentenone ether and 4,5-dibenzylcyclopentenone ether were confirmed by nuclear magnetic resonance (NMR) using a nuclear magnetic resonance apparatus JNM-EX270 FT NMR system (Nippon Denshi). The chemical shift values in $^1$H-NMR are expressed assuming the chemical shift value of tetramethylsilane as 0 ppm. The results are shown below.

4-Benzylcyclopentenone ether $^1$H-NMR; δ7.47 (1H, dd, J=6.0 Hz, J=1.68), δ7.36 (5H, m), δ6.3 (1H, dd, J=6.0 Hz, J=1.33 Hz), δ4.88 (1H, d, J=11.55), δ4.75 (1H, d, J=11.55), δ4.55 (1H, m), δ4.28 (1H, m), δ2.78 (1H, m).

5-Benzylcyclopentenone Ether $^1$H-NMR; δ7.39 (6H, m), δ6.22 (1H, dd, J=6.24 Hz, J=1.32 Hz), δ5.09 (1H, d, J=11.87), δ4.79 (1H, m), δ4.77 (1H, d, J=11.87), δ3.98 (1H, d, J=2.97), δ2.06 (1H, m).

4,5-Dibenzylcyclopentenone Ether $^1$H-NMR; δ7.47 (1H, dd, J=6.27 Hz, J=1.98), δ7.34 (10H, m), δ6.29 (1H, dd, J=6.10 Hz, J=1.49 Hz), δ4.88 (1H, d, J=11.85), δ4.74 (1H, d, J=11.85), δ4.71 (2H, d, J=11.55), δ4.56 (1H, m), δ4.33 (1H, d, J=2.64).

(22) 44 mg of cyclopentenone and 287 mg of t-butyl 2,2,2-trichloroacetimidate (Aldrich, 36,478-9) was dissolved in 2.5 ml of dichloromethane under argon flow. 1 ml of 28 μl/ml boron trifluoride diethyl ether complex solution in dichloromethane was slowly added thereto while stirring.

After stirring for 8 hours at room temperature, the mixture was concentrated under reduced pressure. The concentrate was subjected to silica gel thin-layer chromatography to purify 4-t-butylcyclopentenone ether, 5-t-butylcyclopentenone ether and 4,5-di-t-butylcyclopentenone ether as described in Referential Example 1-(21). The Rf values for 4-t-butylcyclopentenone ether, 5-t-butylcyclopentenone ether and 4,5-di-t-butylcyclopentenone ether were 0.35, 0.27 and 0.73, respectively. The yields of 4-t-butylcyclopentenone ether, 5-t-butylcyclopentenone ether and 4,5-di-t-butylcyclopentenone ether were 9.2%, 1.9% and 11%, respectively.

Structures of 4-t-butylcyclopentenone ether, 5-t-butylcyclopentenone ether and 4,5-di-t-butylcyclopentenone ether were confirmed by NMR as described in Referential Example 1-(21). The results are shown below.

4-t-Butylcyclopentenone Ether $^1$H-NMR; δ7.34 (1H, dd, J=5.94 Hz, J=0.99), δ6.25 (1H, dd, J=6.10, J=1.49), δ4.59 (1H, m), 64.08 (1H, d, J=2.31), δ2.85 (1H, m), δ1.33 (9H, s).

5-t-Butylcyclopentenone Ether $^1$H-NMR; δ7.37 (1H, dd, J=6.27 Hz, J=1.98), δ6.23 (1H, dd, J=6.27, J=1.32), δ4.75 (1H, m), δ4.04 (1H, d, J=2.63), δ2.23 (1H, m), δ1.32 (9H, s).

4,5-Di-t-butylcyclopentenone Ether $^1$H-NMR; δ7.35 (1H, dd, J=6.27 Hz, J=1.65), δ6.24 (1H, dd, J=6.26, J=0.99), δ4.62 (1H, ddd, J=3.3, J=1.65, J=0.99), δ4.16 (1H, d, J=3.31), δ1.38 (18H, s).

(23) 100 μl of 1M aqueous cyclopentenone solution and 500 μl of 200 mM aqueous glutathione (reduced; Nacalai Tesque, 170-10) solution (pH 3.0) were mixed together. The mixture was reacted at 60° C. for 5 hours. The reaction mixture was filtrated through a 0.5-μm Cosmonice filter and separated on HPLC under the following conditions.

Column: TSKgel ODS-80Ts (5 μm) 20 mm×25 cm;

Mobile Phase A: 0.1% aqueous TFA solution;

B: aqueous solution containing 0.1% TFA/50% acetonitrile;

Flow rate: 7.5 ml/min.;

Gradient: Mobile Phase A (10 min.)→Mobile Phase A to A:B=1:1 (55 min.)→A:B=1:1 to Mobile Phase B (15 min.);

Detection: absorbance at 220 nm.

200 μl of the reaction mixture was subjected to HPLC. Peaks at retention time of 35.7 min. and 36.1 min. were collected and evaporated to dryness under reduced pressure to obtain 5.5 mg of dry solid.

The structure of the dry solid was analyzed. Measurements were carried out using JNM-A500 for NMR spectrum, DX302 mass spectrometer (Nippon Denshi) for mass spectrum (MS), UV-2500 spectrophotometer (Shimadzu) for ultraviolet (UV) absorption spectrum and FTIR-8000PC infrared spectrometer (Shimadzu) for infrared absorption (IR) spectrum, respectively. The results are shown below.

$^1$H-NMR; δ2.09 (2H, m, 5'-H), 2.28 (1H, dd, J=13.0, 20.0 Hz, 5-H), 2.44 (2H, m, 4'-H), 2.78 (1H, dd, J=8.5, 14.0, 1'-H), 2.85 or 2.89 (1H, dd, J=3.0, 6.0 Hz, 5-H), 2.92 or 2.95 (1H, dd, J=1.0, 5.5 Hz, 1'-H), 3.86 (2H, S, 9'-H), 3.95 (2H, m, 4-H, 6'-H), 4.46 (1H, m, 2'-H), 6.47 or 6.49 (1H, d, J=3.0 Hz, 3-H).

The sample was dissolved in 0.1 N DCl solution in heavy water. The results are expressed assuming the chemical shift value of HOD as 4.65 ppm.

$^{13}$C-NMR; δ26.3 (5'-C), 31.7 (4'-C), 31.9 or 32.1 (1'-C), 39.3 (4-C), 41.9 (9'-C), 42.2 or 42.3 (5-C), 53.3 (6'-C), 54.1 (2'-C), 133.5 (3-C), 154.4 (2-C), around 173 (3'-C, 7'-C, 8'-C, 10'-C), 205.8 (1-C).

The sample was dissolved in 0.1 N DCl solution in heavy water. The results are expressed assuming the chemical shift value of dioxane as 67.4 ppm.

The numbers for peak identification in $^1$H-NMR and $^{13}$C-NMR are as indicated in formula [X] below.

[X]

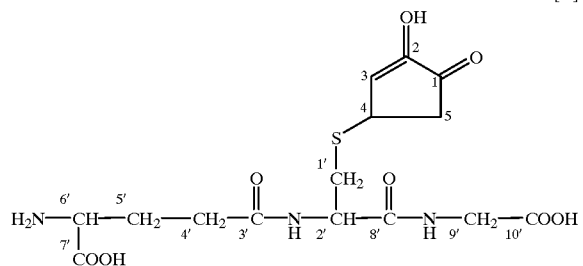

FAB-MS; m/z 404 (M+H)$^+$, 426 (M+Na)$^+$.
Glycerol was used for matrix.
UV λ$_{max}$ 251 nm (water) IR ν$^{KBr}_{max}$ cm$^{-1}$ 2949, 1710, 1660, 1539, 1404, 1203.

Measurement was carried out according to diffuse reflectance method.

These results revealed that the dry solid was 2-hydroxy-4-glutathion-S-yl-2-cyclopenten-1-one.

(24) Therapeutic effects of cyclopentenone and 2-hydroxy-4-glutathion-S-yl-2-cyclopenten-1-one were examined by conducting experiments in which mice were infected with influenza virus.

Each of 4 weeks old female BALB/c mice was intranasally infected with 1×10$^4$ FFU of human influenza virus A1/FM/1/47 (ATCC VR-97) which had been propagated in a hen's egg.

Immediately after the infection with virus, single dose of 1 mg/kg of cyclopentenone, or 3 mg/kg or 30 mg/kg of 2-hydroxy-4-glutathion-S-yl-2-cyclopenten-1-one was intraperitoneally administered to the mouse infected with influenza virus.

Phosphate buffered saline was administered to control mice.

As a result, 4 out of 11 mice in the control group died by day 16. On the other hand, the numbers of dead mice were only 1 out of 11, 1 out of 11 and 1 out of 10 for the groups administered with 1 mg/kg of cyclopentenone, 3 mg/kg of 2-hydroxy-4-glutathion-S-yl-2-cyclopenten-1-one and 30 mg/kg of 2-hydroxy-4-glutathion-S-yl-2-cyclopenten-1-one, respectively. Thus, the anti-influenza viral activities due to the administration with cyclopentenone or 2-hydroxy-4-glutathion-S-yl-2-cyclopenten-1-one were demonstrated.

EXAMPLE 1

(1) 13 mg of dihexanoylcyclopentenone obtained in Referential Example 1-(9) was dissolved in 300 μl of ethanol. 700 μl of phosphate buffered saline (PBS; Takara Shuzo, T900) and 13 mg of glutathione (reduced; Nacalai Tesque, 170-50) were added thereto. 150 μl of 1 M Tris-HCl (pH 7.5) was further added thereto to adjust the pH to about 7. The mixture was reacted at room temperature for 30 hours and subjected to silica gel column chromatography using ethyl acetate:acetic acid:water=13:4:4 as a mobile phase to obtain a fraction that results in a spot at Rf=0.2 on silica gel thin-layer chromatography using the mobile phase as a developing solvent. The solvent was removed by evaporating under reduced pressure to obtain 12 mg of reaction product.

(2) Structure of the reaction product obtained in Example 1-(1) was analyzed. Measurements were carried out using JNM-A500 (Nippon Denshi) for nuclear magnetic resonance (NMR) spectrum, DX302 mass spectrometer (Nippon Denshi) for mass spectrum (MS), UV-2500 spectrophotometer (Shimadzu) for ultraviolet (UV) absorption spectrum and FTIR-8000PC infrared spectrometer (Shimadzu) for infrared absorption (IR) spectrum, respectively.

The results are shown below.

$^1$H-NMR; δ0.86 (3H, t, J=7.0 Hz, 11-H), 1.29 (4H, m, 10-H, 9-H), 1.57 (2H, m, 8-H), 1.89 (2H, m, 6'-H), 2.33 (3H, m, 5'-H, 5-H), 2.52 (2H, m, 7-H), 2.72 (1H, dd, J=10.0, 13.0 Hz, 1'-H) or 2.79 (1H, dd, J=9.5, 13.5 Hz, 1'-H), 2.99 (2H, m, 1'-H, 5-H), 3.32 (1H, m, 7'-H), 3.70 (2H, m, 11'-H), 4.22 (1H, m, 4-H), 4.48 (1H, m, 2'-H), 7.46 (1H, d, J=3.0 Hz, 3-H) or 7.47 (1H, d, J=2.5 Hz, 3-H), 8.47 (1H, m, 3'-H), 8.70 (1H, m, 10'-H).

The sample was dissolved in heavy dimethyl sulfoxide. The results are expressed assuming the chemical shift value of the residual proton of heavy dimethyl sulfoxide as 2.49 ppm $^{13}$C-NMR; δ13.7 (11-C), 21.7 (9-C or 10-C), 23.9 (8-C), 26.8 (6'-C), 30.4 (9-C or 10-C), 31.4 (5-C), 32.4 (1'-C) or 32.6 (1'-C), 32.9 (7-C), 38.0 (4-C) or 38.1 (4-C), 41.0 (5-C) or 41.19 (5-C), 41.23 (11'-C), 52.3 (2'-C) or 52.6 (2'-C), 53.1 (7'-C), 146.7 (3-C), 148.95 (2-C) or 149.00 (2-C), 169.9 (6-C), 170.4 (8'-C), 170.6 (9'-C), 171.0 (12'-C), 171.8 (4'-C), 198.3 (1-C) or 198.4 (1-C).

The sample was dissolved in heavy dimethyl sulfoxide. The results are expressed assuming the chemical shift value of heavy dimethyl sulfoxide as 39.5 ppm The numbers for peak identification in $^1$H-NMR and $^{13}$C-NMR are as indicated in formula [XI] below.

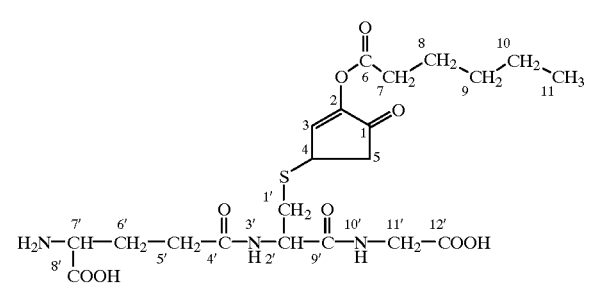

FAB-MS; m/z 502 [M+H]$^+$524 [M+Na]$^+$m-Nitrobenzyl alcohol was used for matrix.

UV λ$_{max}$ 227, 273 nm (MeOH) IR ν$_{max}$ cm$^{-1}$ 3359, 2933, 1768, 1730, 1647, 1517, 1236, 1103.

Measurement was carried out according to diffuse reflectance method.

These results revealed that the reaction product was 2-hexanoyloxy-4-glutathion-S-yl-2-cyclopenten-1-one of formula [VIII] (hereinafter simply referred to as hexanoyl GM), which is the cyclopentenone thio derivative of the present invention. The cyclopentenone thio derivative was a mixture of two diastereomers. The respective diastereomers were separated from the reaction product.

Figure 2:
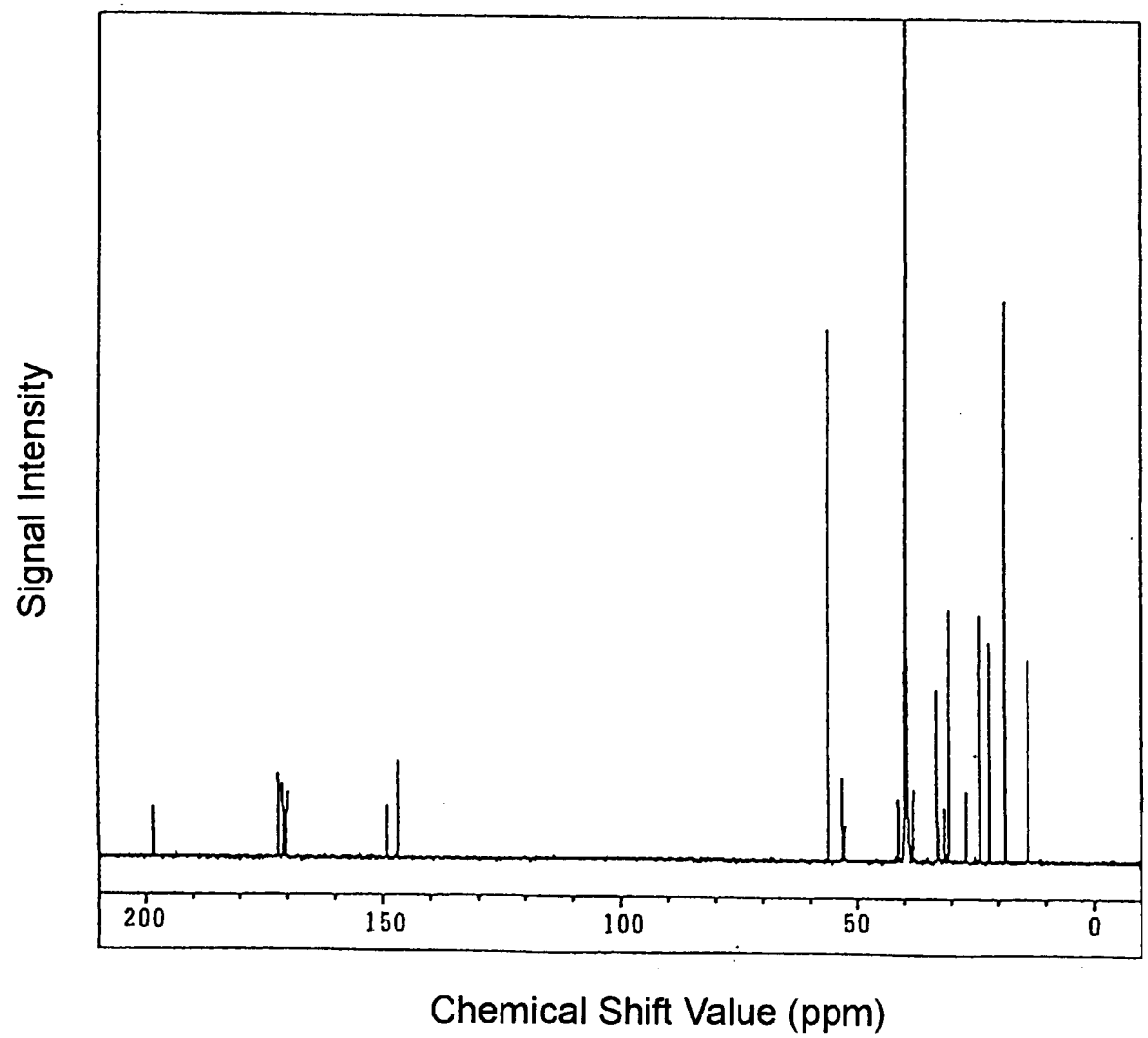
FIG. 2 illustrates the $^{13}$C-NMR spectrum of hexanoyl GM.
Figure 3:
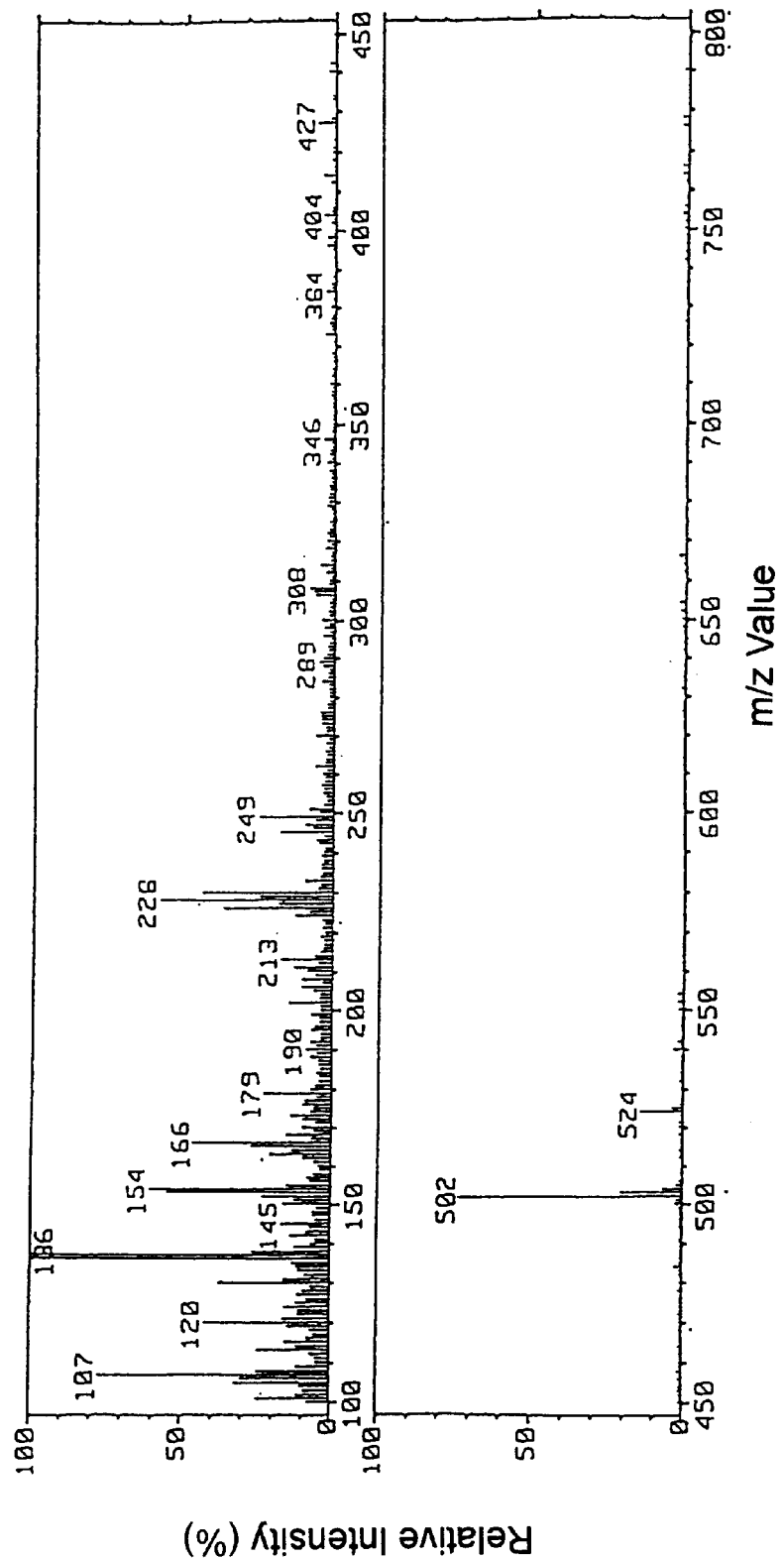
FIG. 3 illustrates the mass spectrum of hexanoyl GM.
Figure 4:
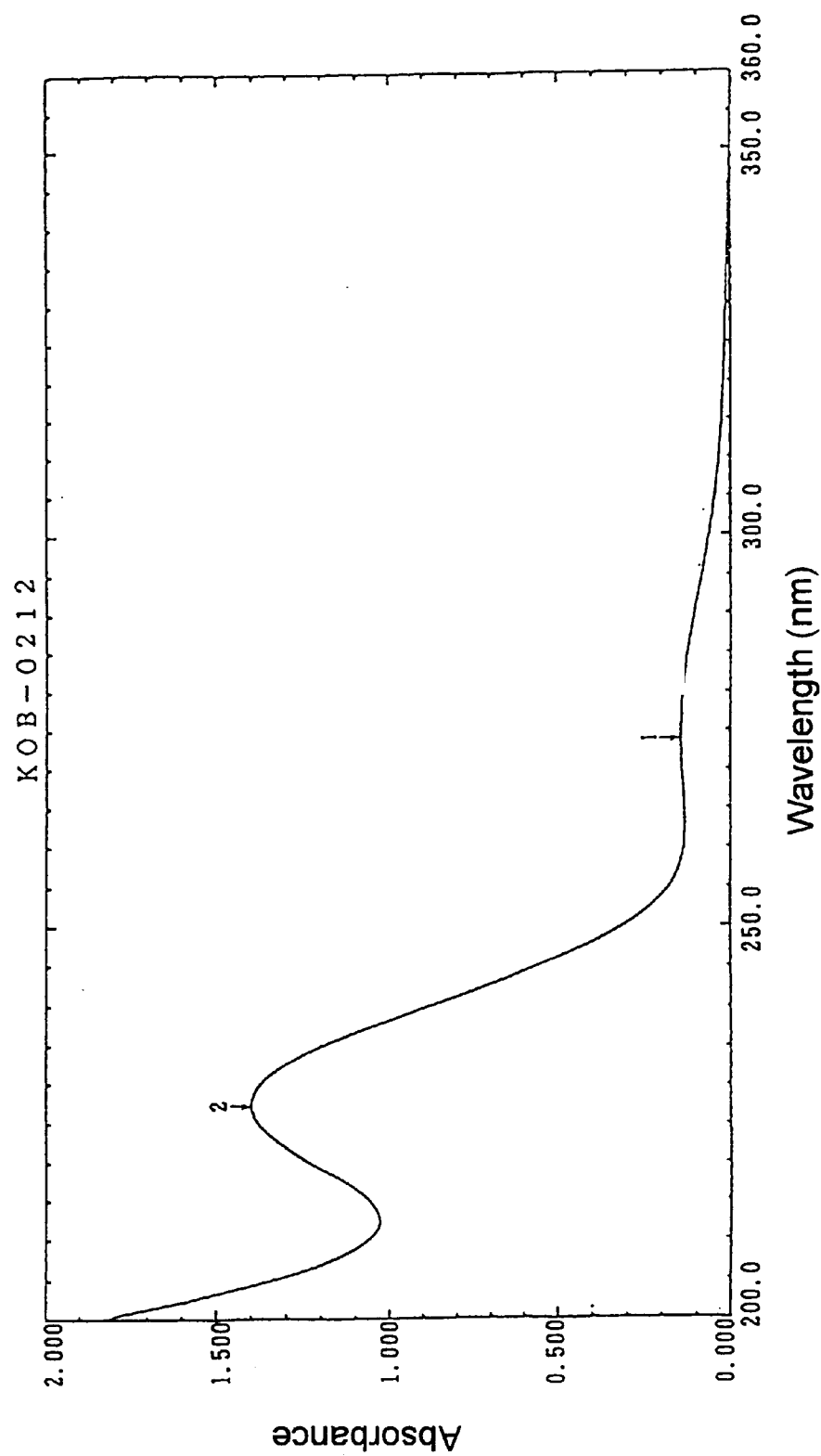
FIG. 4 illustrates the UV absorption spectrum of hexanoyl GM.
Figure 5:
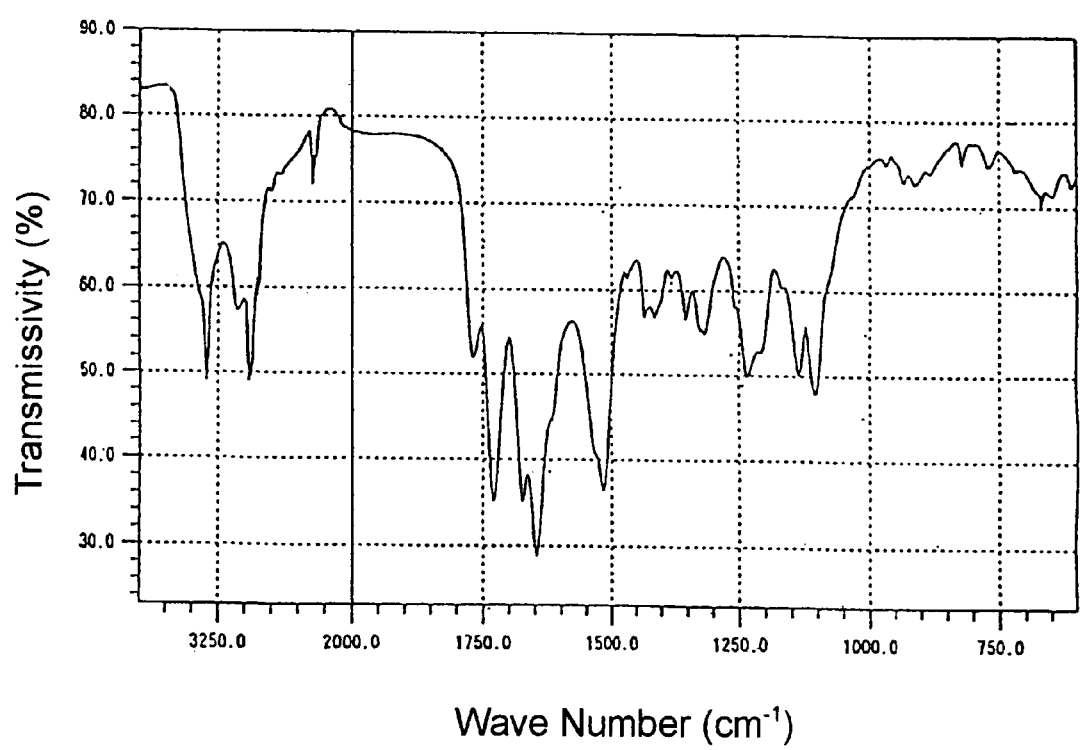
FIG. 5 illustrates the IR absorption spectrum of hexanoyl GM.

The analytical results for hexanoyl GM are shown in FIGS. 1–5. FIG. 1 illustrates the $^1$H-NMR spectrum of hexanoyl GM. The horizontal axis represents the chemical shift value (ppm) and the vertical axis represents the signal intensity. FIG. 2 illustrates the $^{13}$C-NMR spectrum of hexanoyl GM. The horizontal axis represents the chemical shift value (ppm) and the vertical axis represents the signal intensity. FIG. 3 illustrates the mass spectrum of hexanoyl GM. The horizontal axis represents the m/z value and the vertical axis represents the relative intensity (%). FIG. 4 illustrates the UV absorption spectrum of hexanoyl GM. The horizontal axis represents the wavelength (nm) and the vertical axis represents the absorbance. FIG. 5 illustrates the IR absorption spectrum of hexanoyl GM. The horizontal axis represents the wave number (cm$^{-1}$) and the vertical axis represents the transmissivity (%).

EXAMPLE 2

(1) 185 mg of 4,5-di-t-butylcyclopentenone ether obtained in Referential Example 1-(22) was dissolved in 3.6 ml of ethanol. 3.6 ml of PBS and 252 mg of glutathione (reduced) were added thereto. 1 M Tris-HCl (pH 7.5) was further added thereto to adjust the pH to about 7. The mixture was then reacted at room temperature for 1 hour.

The reaction mixture was evaporated to dryness under reduced pressure and subjected to silica gel column chromatography using ethanol:acetic acid:water=3:1:1 as a mobile phase to obtain a fraction that results in a spot at Rf=0.3 on silica gel thin-layer chromatography using ethanol:acetic acid:water=3:2:2 as a developing solvent. 4,5-di-t-butylcyclopentenone ether can be detected by orcinol-sulfuric acid method and glutathione (reduced) can be detected by ninhydrin method on silica gel thin-layer chromatography. Thus, the spot at Rf=0.3 for the reaction product can be detected by both of these methods. The fraction was concentrated under reduced pressure. Hexane was added thereto to precipitate white powder. Thus, 240 mg of a reaction product was obtained.

(2) $^1$H-NMR spectrum and mass spectrum of the reaction product obtained in Example 2-(1) were measured using JNM-500 nuclear magnetic resonance apparatus (Nippon Denshi) and DX302 mass spectrometer. As a result, the reaction product was revealed to be 2,3-di-t-butoxy-4-glutathion-S-yl-1-cyclopentanone of formula [IX] (hereinafter simply referred to as di-t-butyl GD), which was a mixture of diastereomers.

FAB-MS; m/z 532 [M–H]$^-$ 554 [M+Na–2H]$^-$

Triethanolamine was used for matrix.

Figure 6:
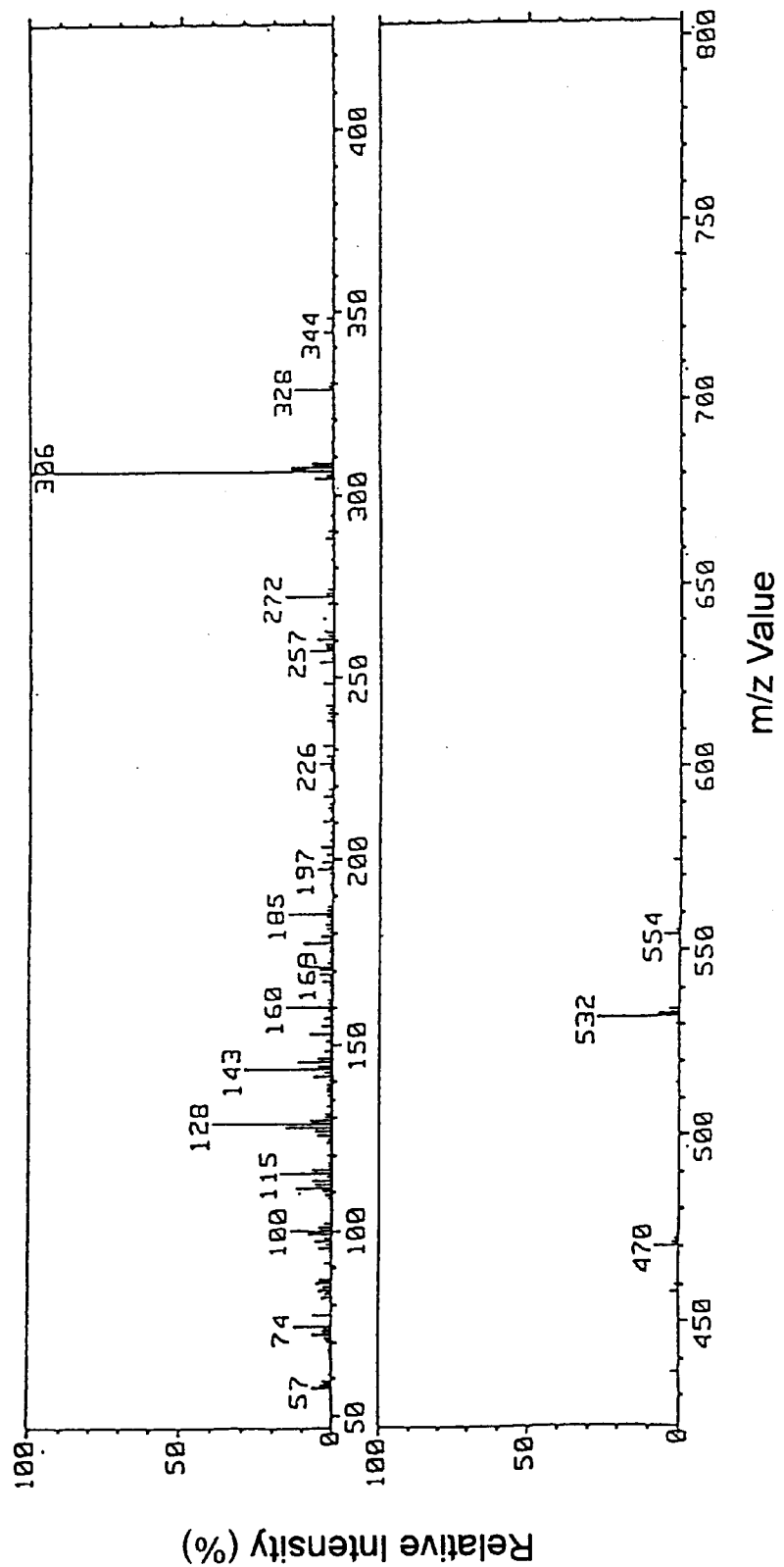
FIG. 6 illustrates the mass spectrum of di-t-butyl GD.

FIG. 6 illustrates the mass spectrum of di-t-butyl GD. In FIG. 6, the horizontal axis represents the m/z value and the vertical axis represents the relative intensity (%)

Figure 7:
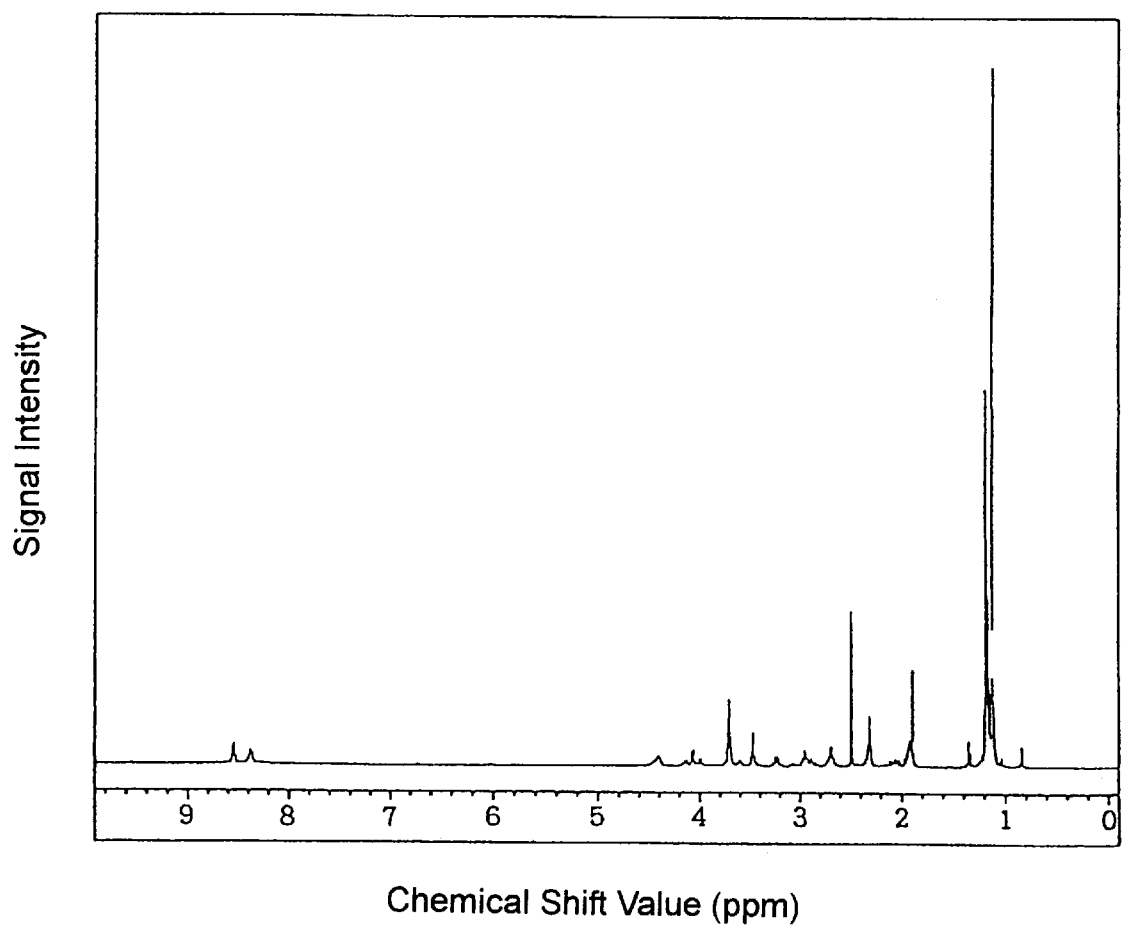
FIG. 7 illustrates the $^1$H-NMR spectrum of di-t-butyl GD.

FIG. 7 illustrates the $^1$H-NMR spectrum of di-t-butyl GD. Heavy dimethyl sulfoxide was used as a solvent. In FIG. 7, the horizontal axis represents the chemical shift value (ppm) and the vertical axis represents the signal intensity.

EXAMPLE 3

(1) 100 μl of a suspension containing HL-60 (ATCC CCL-240) cells in RPMI-1640 medium (Nippon Suisan Kaisha) containing 10% fetal calf serum (Gibco) which had been treated at 56° C. for 30 minutes at a concentration of 5×10$^4$ cells/ml was dispensed into each well of a 96-well microtiter plate. 10 μl of one of 2-fold serial dilutions with water of 8.3 mM hexanoyl GM solution in 25 mM Tris-HCl buffer was added to the well of the plate. The plate was incubated at 37° C. for 48 hours in the presence of 5% CO$_2$. After the cells were examined under an optical microscope, 10 μl of 5 mg/ml 3-(4,5-dimethylthiazol-2-yl)-2,5-diphenyltetrazolium bromide (MTT; Sigma) solution in phosphate buffered saline was added to the well. The plate was incubated for additional 4 hours. 100 μl of 2-propanol containing 0.04 N HCl was added to the well, the mixture was stirred, and the absorbance at 590 nm was measured.

As a result, hexanoyl GM at a final concentration down to 6.25 pm clearly exhibited an antiproliferation activity against tumor cells. Additionally, apoptosis corpuscles were observed under an optical microscope, indicating the induction of apoptosis.

(2) 10 μl of one of 2-fold serial dilutions with 70% aqueous ethanol solution of 19 mM di-t-butyl GD solution in 70% aqueous ethanol solution was added to each well of a 96-well microtiter plate and air-dried. 100 μl of HL-60 suspension was then dispensed as described above. An apoptosis-inducing activity and an antiproliferation activity against tumor cells were examined using a measurement system using MTT.

As a result, di-t-butyl GD at a final concentration down to 34 μM clearly exhibited an antiproliferation activity against tumor cells. Additionally, apoptosis corpuscles were observed under an optical microscope, indicating the induction of apoptosis.

(3) HL-60 cells were cultured at 37° C. in RPMI 1640 medium (Bio Whittaker) containing 10% fetal calf serum (JRH) which had been treated at 56° C. for 30 minutes and suspended in RPMI 1640 medium at a concentration of 2.5×10$^5$ cells/5 ml.

10 μl of one of appropriate dilutions of the hexanoyl GM solutions in 20 mM Tris-HCl buffer or the di-t-butyl GD solution in 70% aqueous ethanol solution was added to 5 ml of the suspension. The mixtures were incubated at 37° C. for 24 hours in the presence of 5% CO$_2$. 10 μl of aqueous actinomycin D (Sigma) solution (0.5 mg/ml), which is known as a reagent that induces apoptosis, was used in place of the sample and the mixture was incubated under the same conditions for confirmation.

The cultured cells were examined under an optical microscope. Condensation of nuclei, shrinking of cells and formation of apoptosis corpuscles were observed for the cells cultured with the addition of the samples and actinomycin D. No such phenomenon was observed for the control cells cultured with the addition of 10 μl of saline or 70% ethanol.

Furthermore, a portion of the cells cultured for 24 hours as described above was stained with 0.4% Trypan Blue and examined under an optical microscope. The number of viable cells which were not stained and the number of dead cells which were stained blue were counted. The concentration of each of the samples that results in a viability of 50% (Viability$_{50}$ μM) was determined. As a result, Viability$_{50}$ for hexanoyl GM was 9.22 μM and that for di-t-butyl GD was 46.3 μM.

Measurement of apoptotic cells using FACScan as described in Saibo Kogaku, Bessatsu (Cell Technology, Suppl.) Jikken Protocol Series: Apoptosis Jikken Protocol (Experimental Protocol Series: Experimental Protocols for Apoptosis) (Shujun-sha) pp. 129–130 and analysis of DNA fragmentation as described in Bio Manual UP Series: Saishin Apoptosis Jikken-ho (Bio Manual UP Series: Current Experimental Methods for Apoptosis) (Yodo-sha) pp. 61–63 were carried out using cells cultured in the same manner as that described above. As a result, apoptotic cells and DNA fragmentation were observed for the cells cultured with the addition of the samples and actinomycin D. No such phenomenon was observed for the control cells cultured with the addition of 10 μl of saline or 70% ethanol.

EXAMPLE 3

(1) 2 μl of topoisomerase II (TopoGEN; 2 units/μl), 2 μl of 10-fold concentrated buffer [0.5 M Tris-HCl (pH 8.0), 1.2 M KCl, 0.1 M $MgCl_2$, 5 mM adenosine triphosphate, 5 mM dithiothreitol], 2 μl of 0.1% bovine serum albumin (Takara Shuzo), 11 μl of distilled water and 2 μl of distilled water (control) or 2 μl of one solutions of hexanoyl GM adjusted to varying concentrations with water were mixed together. 1 μl of 0.25 μg/μl pBR322 DNA (Takara Shuzo) was added thereto. The resulting mixture was reacted at 37° C. After reacting for 30 minutes, 2 μl of an aqueous solution containing 1% sodium dodecyl sulfate, 50% glycerol and 0.02% Bromophenol Blue was added thereto to stop the reaction.

20 μl of the reaction mixture was applied to 1% agarose gel prepared using agarose L03 (Takara Shuzo) and TAE buffer [40 mM Tris, 5 mM sodium acetate, 1 mM ethylenediaminetetraacetic acid disodium salt; adjusted to pH 7.8 using acetic acid] and electrophoresed in TAE buffer. After electrophoresis, the gel was soaked in a 1 μg/ml aqueous ethidium bromide solution. The gel was exposed to ultraviolet rays to visualize the electophoretic pattern of DNA. The form of DNA is completely changed from superhelical type to relaxed type for a control to which water is added, whereas the change from superhelical type to relaxed type is partially or completely inhibited if topoisomerase II activity is inhibited.

As a result, the form of DNA was completely changed from superhelical type to relaxed type for a control to which water was added. On the other hand, the change in the form of the DNA from superhelical type to relaxed type was partially or completely inhibited by hexanoyl GM at a concentration of 100 μM or more, confirming the activity of inhibiting topoisomerase II of hexanoyl GM.

(2) The activity of inhibiting topoisomerase I of hexanoyl GM was determined as described in Example 3-(1) except that topoisomerase I (TopoGEN; 0.01 unit/μl) was used in place of topoisomerase II and a solution containing 100 mM Tris-HCl (pH 7.9), 10 mM EDTA, 1 mM spermidine and 50% glycerol was used as 10-fold concentrated buffer.

As a result, the form of DNA was completely changed from superhelical type to relaxed type for a control to which water was added. On the other hand, the change in the form of the DNA from superhelical type to relaxed type was partially inhibited by hexanoyl GM at a concentration of 1000 μM or more, confirming the activity of inhibiting topoisomerase I of hexanoyl GM.

As described above, hexanoyl GM exhibited a selective inhibitory activity on topoisomerase II as compared with the activity on topoisomerase I. Topoisomerase II is transiently expressed only during division phase in normal cells, whereas it is highly expressed throughout the cell cycle when cells cancerate. The expression level and activity of topoisomerase I are increased upon canceration.

EXAMPLE 4

Injectable Preparation

Hexanoyl GM was added to saline (described in The Pharmacopoeia of Japan) at a concentration of 0.1% to prepare injectable preparations.

Tablet

Tablets each containing 100 mg of di-t-butyl GD and a suitable amount of crystallite cellulose were prepared and sugar-coated.

| Ointment | |
|---|---|
| Hexanoyl GM | 1 g |
| Absorptive ointment | 99 g |

Hexanoyl GM was first thoroughly kneaded with a small amount of absorptive ointment. The remaining absorptive ointment was slowly added thereto. The mixture was kneaded to homogeneity to prepare ointment.

This ointment is applied to a diseased part 4 to 5 times a day.

As described above, the present invention provides a specific five-membered ring compound or an optical isomer thereof, or a salt thereof having various physiological activities such as a carcinostatic activity, an antiproliferation activity against tumor cells and an apoptosis-inducing activity. The present invention also provides a pharmaceutical composition containing at least one compound selected from these compounds as its active ingredient. The pharmaceutical composition is useful as a pharmaceutical composition for treating or preventing diseases sensitive to the compound, in particular as a carcinostatic composition.

Furthermore, a suitable amount of the compound of the present invention or an optical isomer thereof, or a salt thereof, which has a physiological activity, can be contained in a food or a drink according to the present invention. Based on the various physiological activities of the compounds such as a carcinostatic activity and an apoptosis-inducing activity, the foods or drinks provided by the present invention serve as healthy foods or drinks having functions of maintaining homeostasis in a living body such as an effect of preventing carcinogenesis, a carcinostatic effect and an apoptosis-inducing activity. Thus, the present invention provides a food or drink containing a functional substance useful for keeping gastrointestinal health.

What is claimed is:
1. A five-membered ring compound of formula [I]:

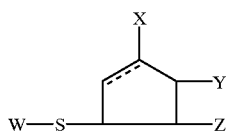

[I]

wherein the bond in the five-membered ring represented by a broken line means that the five-membered ring may be either a cyclopentene ring having a double bond or a saturated cyclopentane ring; if the five-membered ring is a cyclopentene ring, X is $OR_1$, Y is =O and Z is H; if the five-membered ring is a cyclopentane ring, X is =O, Y is $OR_2$ and Z is $OR_3$; $R_1$ is $R_4$ or —(CO)—$R_5$; $R_2$ is H, $R_6$ or —(CO)—$R_7$; and $R_3$ is H, $R_8$ or (CO)—$R_9$ (wherein $R_4$, $R_5$, $R_6$, $R_7$, $R_8$ and $R_9$ may be identical or different each other, and are an aliphatic group, an aromatic group or an aromatic aliphatic group, and $R_5$, $R_7$ and $R_9$ may be H), provided that $R_2$ and $R_3$ are not simultaneously H; and W is a residue in which an SH group is removed from an SH group-containing compound, or an optical isomer thereof, or a salt thereof.

2. A pharmaceutical composition which contains as an active ingredient at least one compound selected from the group consisting of the five-membered ring compound or an optical isomer thereof, and a salt thereof according to claim 1.

3. The pharmaceutical composition according to claim 2, which is a carcinostatic composition.

4. The pharmaceutical composition according to claim 2, which is a composition for inducing apoptosis.

5. A method for producing a five-membered ring compound of formula [I]:

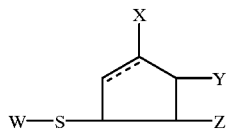

wherein the bond in the five-membered ring represented by a broken line means that the five-membered ring may be either a cyclopentene ring having a double bond or a saturated cyclopentane ring; if the five-membered ring is a cyclopentene ring, X is $OR_1$, Y is $=O$ and Z is H; if the five-membered ring is a cyclopentane ring, X is $=O$, Y is $OR_2$ and Z is $OR_3$; $R_1$ is $R_4$ or —(CO)—$R_5$; $R_2$ is H, $R_6$ or —(CO)—$R_7$; and $R_3$ is H, $R_8$ or (CO)—$R_9$ (wherein $R_4$, $R_5$, $R_6$, $R_7$, $R_8$ and $R_9$ may be identical or different each other and are an aliphatic group, an aromatic group or an aromatic aliphatic group, and $R_5$, $R_7$ and $R_9$ may be H), provided that $R_2$ and $R_3$ are not simultaneously H; and W is a residue in which an SH group is removed from an SH group-containing compound, or an optical isomer thereof, or a salt thereof, characterized in that the method comprises reacting an SH-group containing compound with a compound selected from the group consisting of a compound of formula [II]:

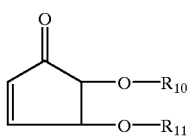

wherein $R_{10}$ is H, $R_{12}$ or —(CO)—$R_{13}$; $R_{11}$ is H, $R_{14}$ or —(CO)—$R_{15}$; (wherein $R_{12}$, $R_{13}$, $R_{14}$ and $R_{15}$ may be identical or different each other, and are an aliphatic group, an aromatic group or an aromatic aliphatic group, and $R_{13}$ and $R_{15}$ may be H), provided that $R_{10}$ and $R_{11}$ are not simultaneously H, or an optical isomer thereof, and a salt thereof.

* * * * *